(12) United States Patent
Kane

(10) Patent No.: US 11,890,200 B2
(45) Date of Patent: Feb. 6, 2024

(54) SURFACE TEXTURES FOR THREE-DIMENSIONAL POROUS STRUCTURES FOR BONE INGROWTH AND METHODS FOR PRODUCING

(71) Applicant: DePuy Ireland Unlimited Company, Ringaskiddy (IE)

(72) Inventor: Robert J. Kane, Warsaw, IN (US)

(73) Assignee: DePuy Ireland Unlimited Company

( * ) Notice: Subject to any disclaimer, the term of this patent is extended or adjusted under 35 U.S.C. 154(b) by 236 days.

(21) Appl. No.: 16/370,538

(22) Filed: Mar. 29, 2019

(65) Prior Publication Data

US 2019/0298533 A1 Oct. 3, 2019

Related U.S. Application Data

(60) Provisional application No. 62/650,775, filed on Mar. 30, 2018.

(51) Int. Cl.
*A61F 2/30* (2006.01)
*A61F 2/38* (2006.01)
*A61L 27/56* (2006.01)

(52) U.S. Cl.
CPC .......... *A61F 2/389* (2013.01); *A61F 2/30767* (2013.01); *A61F 2/30771* (2013.01); *A61L 27/56* (2013.01); *A61F 2002/30011* (2013.01); *A61F 2002/3093* (2013.01); *A61F 2002/30594* (2013.01); *A61F 2002/30838* (2013.01); *A61F 2002/30841* (2013.01); *A61F 2002/30985* (2013.01)

(58) Field of Classification Search
CPC .. A61F 2/389; A61F 2/30767; A61F 2/30771; A61F 2002/30011; A61F 2002/30594; A61F 2002/30838; A61F 2002/30841; A61F 2002/3093; A61F 2002/30985; A61L 27/56; A61L 2430/24; A61L 27/306; A61L 27/58; A61L 2430/02
See application file for complete search history.

(56) References Cited

U.S. PATENT DOCUMENTS

| | | | |
|---|---|---|---|
| 4,038,703 | A | 8/1977 | Bokros |
| 4,479,271 | A | 10/1984 | Bolesky et al. |

(Continued)

FOREIGN PATENT DOCUMENTS

| | | |
|---|---|---|
| EP | 1800700 A2 | 6/2007 |
| EP | 1459845 B1 | 12/2007 |

(Continued)

OTHER PUBLICATIONS

Bobyn et al, Characteristics of bone ingrowth and interface mechanics of a new porous tantalum biomaterial; The Journal of Bone & Joint Surgery, vol. 81-B, No. 5, Sep. 1999, 907-914.

(Continued)

*Primary Examiner* — Brian A Dukert
*Assistant Examiner* — Melissa A Hoban
(74) *Attorney, Agent, or Firm* — BakerHostetler

(57) ABSTRACT

In one aspect, an orthopaedic prosthetic component is provided. The prosthetic component comprises a base, a porous three-dimensional structure and at least one surface feature extending past a surface boundary of the porous three-dimensional structure to engage a patient's bone.

20 Claims, 9 Drawing Sheets

(56) References Cited

U.S. PATENT DOCUMENTS

| | | | |
|---|---|---|---|
| 4,795,472 | A | 1/1989 | Crowninshield et al. |
| 4,842,517 | A | 6/1989 | Kawahara et al. |
| 4,938,769 | A | 7/1990 | Shaw |
| 4,997,445 | A | 3/1991 | Hodorek |
| 5,387,243 | A | 2/1995 | Devanathan |
| 5,534,030 | A | 7/1996 | Navarro et al. |
| 5,534,032 | A | 7/1996 | Hodorek |
| 5,609,641 | A | 3/1997 | Johnson et al. |
| 5,702,484 | A | 12/1997 | Goymann et al. |
| 5,716,358 | A | 2/1998 | Ochoa et al. |
| 5,723,011 | A | 3/1998 | Devanathan et al. |
| 6,027,682 | A | 2/2000 | Almquist et al. |
| 6,869,448 | B2 | 3/2005 | Tuke et al. |
| 7,537,664 | B2 | 5/2009 | O'Neill et al. |
| 7,597,715 | B2 | 10/2009 | Brown et al. |
| 8,021,432 | B2 | 9/2011 | Meridew et al. |
| 8,266,780 | B2 | 9/2012 | Bollinger et al. |
| 8,268,099 | B2 | 9/2012 | O'Neill et al. |
| 8,268,100 | B2 | 9/2012 | O'Neill et al. |
| 8,470,047 | B2 | 6/2013 | Hazebrouck et al. |
| 8,556,981 | B2 | 10/2013 | Jones et al. |
| 8,562,348 | B2 | 10/2013 | Collins et al. |
| 8,590,157 | B2 | 11/2013 | Kruth et al. |
| 8,888,862 | B2 | 11/2014 | Mcdonnell et al. |
| 8,992,703 | B2 | 3/2015 | O'Neill et al. |
| 9,180,010 | B2 | 11/2015 | Dong et al. |
| 9,415,137 | B2 * | 8/2016 | Meridew .............. A61L 27/50 |
| 9,456,901 | B2 | 10/2016 | Jones et al. |
| 10,307,260 | B2 | 6/2019 | Heldreth et al. |
| 10,399,147 | B2 | 9/2019 | Scott et al. |
| 10,596,660 | B2 | 3/2020 | Mccarthy et al. |
| 2002/0120344 | A1 | 8/2002 | Meulink et al. |
| 2003/0180171 | A1 | 9/2003 | Artz et al. |
| 2004/0236430 | A1 | 11/2004 | Koch et al. |
| 2009/0216325 | A1 * | 8/2009 | May ................... A61F 2/389 623/11.11 |
| 2010/0298947 | A1 | 11/2010 | Unger |
| 2010/0298950 | A1 | 11/2010 | Mcdonnell et al. |
| 2011/0313532 | A1 * | 12/2011 | Hunt ..................... A61F 2/46 623/18.11 |
| 2012/0232654 | A1 * | 9/2012 | Sharp ................... A61L 27/56 29/428 |
| 2012/0321878 | A1 | 12/2012 | Landon et al. |
| 2013/0030529 | A1 * | 1/2013 | Hunt ............... A61F 2/30771 623/16.11 |
| 2013/0172927 | A1 | 7/2013 | Natarajan et al. |
| 2013/0190873 | A1 * | 7/2013 | Mansmann .......... A61F 2/3872 623/14.12 |
| 2013/0218284 | A1 | 8/2013 | Eickmann et al. |
| 2013/0325129 | A1 | 12/2013 | Huang |
| 2014/0257507 | A1 * | 9/2014 | Wang ................... A61F 2/461 623/20.34 |
| 2014/0288649 | A1 * | 9/2014 | Hunt .................... A61F 2/447 623/16.11 |
| 2016/0331422 | A1 * | 11/2016 | Al Muderis ............ A61F 2/78 |
| 2017/0095337 | A1 | 4/2017 | Pasini et al. |
| 2017/0266007 | A1 | 9/2017 | Gelaude et al. |
| 2018/0193152 | A1 * | 7/2018 | Bauer ................... A61F 2/34 |
| 2018/0228613 | A1 | 8/2018 | Jones et al. |
| 2018/0296350 | A1 * | 10/2018 | Hamzey ............ A61B 17/7208 |
| 2019/0046322 | A1 | 2/2019 | Moore et al. |
| 2019/0151113 | A1 | 5/2019 | Sack |
| 2019/0290441 | A1 * | 9/2019 | Tong ................... A61F 2/389 |
| 2019/0298525 | A1 * | 10/2019 | Wright .............. A61F 2/30767 |
| 2019/0298533 | A1 | 10/2019 | Kane |
| 2020/0036011 | A1 | 1/2020 | Numata et al. |
| 2020/0129670 | A1 | 4/2020 | Landon et al. |
| 2021/0085466 | A1 | 3/2021 | Tong |

FOREIGN PATENT DOCUMENTS

| | | |
|---|---|---|
| EP | 2319462 A1 | 5/2011 |
| EP | 2774580 | 9/2014 |
| JP | 2002-038201 A | 2/2002 |
| JP | 2010-269144 A | 12/2010 |
| JP | 2014-525801 A | 10/2014 |
| RU | 2207825 C1 | 7/2003 |
| RU | 2325191 C1 | 5/2008 |
| WO | 96/23459 A1 | 8/1996 |
| WO | 2002/069851 | 9/2002 |
| WO | 2009/022911 A2 | 2/2009 |

OTHER PUBLICATIONS

Chua et al, Development of a Tissue Engineering Scaffold Structure Library for Rapid Prototyping. Part 1: Investigation and Classification, Int J Adv Manuf Technol, 2003, 21:291-301.

Chua et al, Development of a Tissue Engineering Scaffold Structure Library for Rapid Prototyping. Part 2: Parametric Library and Assembly Program, Int J Adv Manuf Technol, 2003, 21: 302-312.

Hong et al, A New Ti—5Ag Alloy for Customized Prostheses by Three-dimensional Printing (3DPtm), Research Reports, Biomaterials & Bioengineering, J Dent Res 80(3), 2001, 860-863.

Meiners et al, Direct Generation of Metal Parts and Tools by Selective Laser Powder Remelting (SLPR); Fraunhofer Institute for Laser Technology (ILT), 1999, 655-662.

Morgan et al, Direct Metal Laser Re-Melting (DMLR) of 316L Stainless Steel Powder, Part 1: Analysis of Thin Wall Structures, Research in Advanced Technologies Group, Faculty of Engineering, The University of Liverpool, UK, 2001, 276-282.

Morgan et al, Direct Metal Laser Re-Melting of 316L Stainless Steel Powder, Part 2: Analysis of Cubic Primitives, Research in Advanced Technologies Group, Faculty of Engineering, The University of Liverpool, UK, 2001, 283-295.

Morgan et al, Experimental investigation of nanosecond pulsed Nd:YAG laser re-melted pre-placed powder beds, Rapid Prototyping Journal, vol. 7, No. 3, 2001, 159-172.

Morgan et al, High density net shape components by direct laser re-melting of single-phase powders, Journal of Materials Science 37 (2002), 3093-3100.

Mullen et al, Selective Laster Melting: a Unit Cell Approach for the Manufacture of Porous, Titanium, Bone In-Growth Constructs, Suitable for Orthopedic Applications. II. Randomized Structures, Journal of Biomedical Materials Research Part B: Applied Biomaterials, Jan. 2010, 178-188.

Pogson et al, The production of copper parts using DMLR, Rapid Prototyping Journal, vol. 9, No. 5, 2003, 334-343.

Ramos et al, Mechanics of the Selective Laser Raster-Scanning Surface Interaction, Department of Mechanical and Metallurgical Engineering, Pontificia Universidad, Chile, Department of Mechanical Engineering, University of Texas at Austin, Aug. 2003, 559-572.

Williams et al, Selective Laser Sintering Part Strength as a Function of Andrew Number, Scan Rate and Spot Size, Clemson University, 1996, 10 pages.

Williams, et al, Advances in modeling the effects of selected parameters on the SLS process, Rapid Prototyping Journal, vol. 4, No. 2, 1998, 90-100.

Wysocki et al, Laser and Electron Beam Additive Manufacturing Methods of Fabricating Titanium Bone Implants, Applied Sciences, 7, 657, 2017, 20 pages.

Yang et al, the design of scaffolds for use in tissue engineering, Part II. Rapid prototyping techniques, Tissue engineering, Feb. 2002; vol. 8(1), 1-11.

Yang et al, The design of scaffolds for use in tissue engineering. Part I. Traditional factors, Tissue engineering, Dec. 2001; vol. 7(6), 679-689.

Non-final Rejection dated Jan. 20, 2022 in U.S. Appl. No. 17/028,022, filed Sep. 22, 2020, 14 pages.

* cited by examiner

| Type | Feature Width/Height (mm) | Feature Spacing (mm) | Impact Force (# of Coupons Showing Debris) | | |
|---|---|---|---|---|---|
| | | | Low | "Realistic" | High |
| Gription® | - | - | 0 | 0 | 3/3 |
| Spikes | 0.25/0.45 | 1.5 | 0 | 0 | 0 |
| Cones | 0.4/0.4 | 1.5 | 0 | 0 | 0 |
| Dense Triangular Prisms | 0.25/0.4 | 2 | 0 | 0 | 0 |

FIG. 7

| Surface Texture | Feature Height | Feature Spacing | Static CoF |
|---|---|---|---|
| Ti Porocoat ® | - | - | ~0.8 |
| Ti Gription ® | - | - | ~1.1 |
| No Texture | - | - | 0.54 |
| Cones | 0.4mm | 3.5mm | 1.36 |
| Pyramidal Fins | 0.3mm | 1.5mm | 1.02 |
| Triangular Prisms | 0.3mm | 2mm | 1.35 |

SURFACE TEXTURES FOR THREE-DIMENSIONAL POROUS STRUCTURES FOR BONE INGROWTH AND METHODS FOR PRODUCING

This application claims priority to U.S. Provisional App. No. 62/650,775, which was filed on Mar. 30, 2018 and is expressly incorporated herein by reference.

BACKGROUND

The embodiments disclosed herein are generally directed towards surface features for three-dimensional porous structures for bone ingrowth and methods for producing said structures.

The field of rapid prototyping and additive manufacturing has seen many advances over the years, particularly for rapid prototyping of articles such as prototype parts and mold dies. These advances have reduced fabrication cost and time, while increasing accuracy of the finished product, versus conventional machining processes, such as those where materials (e.g., metal) start as a block of material, and are consequently machined down to the finished product.

However, the main focus of rapid prototyping three-dimensional structures has been on increasing density of rapid prototyped structures. Examples of modern rapid prototyping/additive manufacturing techniques include sheet lamination, adhesion bonding, laser sintering (or selective laser sintering), laser melting (or selective laser sintering), photopolymerization, droplet deposition, stereolithography, 3D printing, fused deposition modeling, and 3D plotting. Particularly in the areas of selective laser sintering, selective laser melting and 3D printing, the improvement in the production of high density parts has made those techniques useful in designing and accurately producing articles such as highly dense metal parts.

In the field of tissue engineering, a porous three-dimensional biocompatible scaffold is needed to accommodate mammalian cells and promote their three-dimensional growth and regeneration, and thus can be used for example, as implants/prosthetic components or other prostheses. Furthermore, this scaffold, or ingrowth coating, requires sufficient surface texture to promote stable implant-bone interface essential for rapid and effective bone ingrowth.

Certain past ingrowth coatings have relied on the random presence of particles/beads protruding above the average coating height to provide asperities and increase the initial friction with bone. This can occur with, for example, traditional sintered porous coatings. Other ingrowth coatings, using additive manufacturing technology such as 3D printing, have become commercially available and, for example, use a pattern of cylindrical spikes or hooks extending above the top surface of the ingrowth coating. While these additive manufacturing solutions do increase friction, they are prone to breaking during impaction or can generate significant debris when impacted into bone due to the design attribute and dimensions necessary to achieve proper impaction.

SUMMARY

According to one aspect of the disclosure, an orthopaedic prosthetic component is disclosed. The orthopaedic prosthetic component comprises a base and a porous three-dimensional structure attached to the base. The porous three-dimensional structure is configured to permit bone in-growth and having an outer surface boundary. The orthopaedic prosthetic component also comprises an engagement stud extending outwardly from the outer surface boundary of the porous three-dimensional structure to an outer impact tip configured to engage a patient's bone. A distance is defined between the outer surface boundary and the outer impact tip, the distance being in a range of 0.05 millimeters and 0.30 millimeters.

In some embodiments, the engagement stud may include an elongated body positioned in the porous three-dimensional structure, and an impaction head extending from the elongated body to the outer impact tip. Additionally, in some embodiments, a slot may extend through the elongated body. In some embodiments, the elongated body may extend from a first end attached to the base to a second end attached to the impaction head.

In some embodiments the engagement stud and the base may be a single integral component. In some embodiments, the engagement stud and the porous three-dimensional structure may be a single integral component.

In some embodiments the engagement stud may be one of a plurality of engagement studs extending outwardly from the outer surface boundary of the porous three-dimensional structure. Each engagement stud may have an outer impact tip configured to engage a patient's bone. A distance may defined between the outer surface boundary and each outer impact tip that is in a range of 0.03 millimeters and 0.30 millimeters.

Additionally, in some embodiments, each engagement stud may extend along a central axis, each engagement stud of a first number of engagement studs may be positioned at a first rotational position about its central axis, and each engagement stud of a second number of engagement studs may be positioned at a second rotational position about its central axis. The second rotational position may be different from the first rotational position. In some embodiments the second rotational position may be 90 degrees from the first rotational position.

In some embodiments, the porous three-dimensional structure has a thickness, and a ratio of each distance relative to the thickness may be less than 0.25.

In some embodiments, the base may include a tibial platform configured to receive a tibial insert. Additionally, in some embodiments, an elongated stem may extend from the tibial platform to a distal tip. The elongated stem may be configured to be implanted in a surgically-prepared proximal end of a patient's tibia. In some embodiments, the porous three-dimensional structure may be attached to a distal surface of the tibial platform and the elongated stem extends outwardly through the three-dimensional structure.

According to another aspect, an orthopaedic prosthetic component comprises a base and a porous three-dimensional structure attached to the base. The porous three-dimensional structure is configured to permit bone in-growth and having an outer surface boundary. The orthopaedic prosthetic component also comprises a plurality of engagement studs extending outwardly along a central axis from the outer surface boundary of the porous three-dimensional structure. Each engagement stud has an outer impact tip configured to engage a patient's bone. Each engagement stud of a number of the plurality of engagement studs is rotated about its central axis at an angle from at least one other of the plurality of engagement studs.

In some embodiments, the plurality of engagement studs may be positioned on an imaginary line extending along the outer surface boundary of the porous three-dimensional structure.

In some embodiments, each engagement stud of a first number of engagement studs may be positioned at a first rotational position about its central axis, and each engagement stud of a second number of engagement studs may be positioned at a second rotational position about its central axis. The second rotational position may be different from the first rotational position.

Additionally, in some embodiments, an engagement stud of the first number of engagement studs may alternate with an engagement stud of the second number of engagement studs.

In some embodiments, the base may include a tibial platform configured to receive a tibial insert. Additionally, in some embodiments, an elongated stem may extend from the tibial platform to a distal tip. The elongated stem may be configured to be implanted in a surgically-prepared proximal end of a patient's tibia.

According to another aspect, a method for producing an orthopaedic prosthetic component is disclosed. The method includes depositing and scanning successive layers of metal powders to form a porous three-dimensional structure and to form at least one engagement stud that extends beyond a surface boundary of the porous three-dimensional structure.

According to another aspect of the disclosure, ingrowth coatings or bodies having surface features or textures providing a stable mechanical interlock with bone tissue, allowing for tissue ingrowth are disclosed. Exemplary surface features or textures of an orthopaedic implant/prosthetic component that limit opportunity for the implant to 'hang-up' on the bone, prevent implant seating, and/or reduce the surface area of the implant in immediate contact with surrounding tissue are disclosed. Ingrowth coatings that limit the amount of loose or broken off portions of the coating or surface features that occur either during implantation, service, or extraction are also disclosed.

In one aspect, an orthopaedic implant/prosthetic component is provided. The implant can comprise a base and a porous three-dimensional structure that comprises a plurality of unit cells, and at least one surface feature extending past a surface boundary of the porous three-dimensional structure. The at least one surface feature is anchored to the base and comprises a tip region that terminates at a point.

In some embodiments, the at least one surface feature may be comprised of a plurality of fins that intersect at the point. Additionally, in some embodiments, the tip region may be triangle shaped. In some embodiments, the at least one surface feature may be cone shaped.

In some embodiments, the at least one surface feature and the base may be formed as a single piece.

In some embodiments, the orthopaedic implant/prosthetic component may be comprised of a plurality of surface features. In some embodiments, at least one of the plurality of surface features may be rotated at a central axis to the base at an angle different from at least one other of the plurality of surface features. In some embodiments, the plurality of surface features may be positioned in at least one row across the surface of the porous three-dimension structure.

In some embodiments, the surface features in the at least one row may be rotated at a central axis to the base alternately between at least a first position and a second position in a repeating pattern across the row.

In some embodiments, the surface features in the at least one row may be rotated at a central axis to the base alternately between at least a first position and a second position in a non-repeating pattern across the row.

In some embodiments, the at least one surface feature may be comprised of a harder material than at least one of the base and the porous three-dimensional structure.

In some embodiments, the at least one surface feature may be comprised of a degradable material.

In some embodiments, the porous three-dimensional structure may be comprised of at least two different materials.

In some embodiments, the at least one surface feature may be configured and arranged to increase the static friction of the porous three-dimensional structure.

In some embodiments, the at least one surface feature may have a height, relative to the surface boundary, of between about 30 microns to 1 millimeter.

In some embodiments, the at least one surface feature further may include an opening.

In another aspect, an orthopaedic implant is provided. The implant can comprise a porous three-dimensional structure comprising a plurality of unit cells and at least one surface feature extending past a boundary of the porous three-dimensional structure. The at least one surface feature has an opening and comprises a plurality of fins that intersect at a point.

In some embodiments, the at least one surface feature may be comprised of at least three fins.

In some embodiments, the at least one surface feature may be triangle shaped.

In some embodiments, the at least one surface feature may be cone shaped.

In some embodiments, the orthopaedic implant may further be comprised of a plurality of surface features and a base. In some embodiments, at least one of the plurality of surface features may be rotated at a central axis to the base at an angle different from at least one other of the plurality of surface features. In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

In some embodiments, the orthopaedic implant may further be comprised of a base and at least one surface feature that is anchored to the base and is comprised of a different material from at least one of the base and the porous-three dimensional structure. In some embodiments, the at least one surface feature may be comprised of a harder material than at least one of the base and the porous three-dimensional structure.

In some embodiments, the at least one surface feature may be comprised of a degradable material.

In some embodiments, the porous three-dimensional structure may be comprised of at least two different materials.

In some embodiments, the at least one surface feature may have a height of between about 30 microns and about 1 millimeter relative to the surface boundary.

In yet another aspect, an orthopaedic implant is provided. The implant can comprise a base and a porous three-dimensional structure comprising a plurality of unit cells, and a plurality of surface features extending past a boundary of the porous three-dimensional structure. At least one of the plurality of surface features is rotated about a central axis relative to the base at an angle different from at least one other of the plurality of surface features.

In some embodiments, the at least one surface feature may be comprised of a plurality of fins that intersect at a point. In some embodiments, the at least one surface feature may be comprised of at least three fins.

In some embodiments, the at least one surface feature may be triangle shaped.

In some embodiments, the at least one surface feature may be cone shaped.

In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

In some embodiments, the at least one surface feature may be anchored to the base and comprises a different material from at least one of the base and the porous three-dimensional structure. In some embodiments, the at least one surface features may be comprised of a harder material than at least the base or the porous three-dimensional structure.

In some embodiments, the at least one surface feature may be comprised of a degradable material.

In some embodiments, the porous three-dimensional structure may be comprised of a degradable material.

In some embodiments, the porous three-dimensional structure may be comprised of at least two different materials.

In some embodiments, the at least one surface feature may be configured and arranged to increase the static friction of the porous three-dimensional structure.

In some embodiments, the at least one surface feature may have a height of about 30 microns to about 1 millimeter relative to the surface boundary.

In some embodiments, the at least one surface feature may have an opening.

In some embodiments, the least one of the plurality of surface features may be rotated about a central axis relative to the base at an angle of about 90 degrees from at least one other of the plurality of surface features.

In another aspect, an orthopaedic implant is provided. The implant can include a porous three-dimensional structure comprising a plurality of unit cells and at least one surface feature extending past a surface boundary of the porous three-dimensional structure. Each of the unit cells is further comprised of an outer geometric structure having a first geometry and an inner geometric structure having a second geometry. The outer geometric structure is comprised of first struts. The inner geometric structure is comprised of a plurality of second struts connected to a portion of the plurality of first struts to form the inner geometric structure within the other geometric structure.

In some embodiments, the orthopaedic implant may further be comprised of a base and at least one surface feature that is anchored to the base and is comprised of a triangle shaped region. In some embodiments, the at least one surface feature may further include a tip region that is a triangle shaped region.

In some embodiments, the at least one surface feature may be cone shaped.

In some embodiments, the at least one surface feature and base may be formed as a single piece.

In some embodiments, the orthopaedic implant may further be comprised of a base and a plurality of surface features. In some embodiments, the at least one of the plurality of surface features may be rotated at a central axis to the base at an angle that is different from at least one other of the plurality of surface features. In some embodiments, the plurality of surface features may be positioned in at least one row across the surface of the porous three-dimensional structure. In some embodiments, the surface features in the at least one row may be rotated at a central axis to the base alternatively between at least a first position and a second position in a repeating pattern across the row. In some embodiments, the surface features in the at least one row may be rotated at a central axis to the base alternately between a first or a second position in a non-repeating pattern across the row.

In some embodiments, the at least one surface feature may be comprised of a plurality of fins that intersect at a point. In some embodiments, the at least one surface feature may be comprised of at least three fins.

In some embodiments, the at least one surface feature may be configured and arranged to increase the static friction of the porous three-dimensional structure.

In some embodiments, the at least one surface feature may have a height between about 30 microns and about 1 millimeter relative to the surface boundary.

In some embodiments, the at least one surface feature may have an opening.

In some embodiments, at least one on the plurality of surface features may be rotated at a central axis to the base at an angle of about 90 degrees from at least one other of the plurality of surface features.

In still yet another aspect, a method for producing an orthopaedic implant is provided. The method can comprise depositing and scanning successive layers of metal powders to form a porous three-dimensional structure comprising a plurality of unit cells, and to form at least one surface feature that extends beyond a surface boundary of the porous-three-dimensional structure. The at least one surface feature comprises a tip region that terminates at a point.

In some embodiments, the metal powders may be sintered to form the porous-three dimensional structure.

In some embodiments, the metal powders may be melted to form the porous three-dimensional structure.

In some embodiments, the method for producing the orthopaedic implant may further be comprised of providing a base and forming at least one of the surface features on the base. In some embodiments, a plurality of surface features may be formed on the base. In some embodiments, at least one of the plurality of surface features may be rotated at a central axis to the base at an angle that is different from at least one other of the plurality of surface features. In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between a first position and a second position in a non-repeating pattern across the row.

In some embodiments, the at least one surface feature may be comprised of a harder metal than the porous three-dimensional structure.

In some embodiments, the at least one surface feature may be comprised of a degradable material.

In some embodiments, the porous three-dimensional structure may be comprised of at least two different materials.

In some embodiments, the at least one surface feature may be configured and arranged to increase the static friction of the porous three-dimensional structure.

In another aspect, a method for producing an orthopaedic implant is provided. The method can comprise applying a stream of metal particles at a predetermined velocity onto a base to form a porous three-dimensional structure comprising a plurality of unit cells and to form at least one surface feature that extends beyond a surface boundary of the porous-three-dimensional structure. The at least one surface feature comprises a tip region that terminates at a point.

In some embodiments, the predetermined velocity may be a critical velocity required for the metal particles to bond upon impacting the base. In some embodiments, the critical velocity may be greater than about 340 m/s.

In some embodiments, the method for producing an orthopaedic implant may further include applying a laser at a predetermined power setting onto an area of the base where the stream of metal particles is impacting.

In some embodiments, a plurality of surface features may be formed.

In some embodiments, at least one of the plurality of surface features may be rotated at a central axis to the base at an angle different from at least one other of the plurality of surface features.

In some embodiments, the plurality of surface feature may be position in at least one row across the surface of the porous three-dimensional structure. In some embodiments, the surface features in the at least one row may be rotated at a central axis to the base alternately between at least a first position and a second position in a repeating pattern across the row.

In some embodiments, the surface features in the at least one row may be rotated at a central axis to the base alternately between at least a first position and a second position in a non-repeating pattern across the row.

In some embodiments, the at least one surface feature may be comprised of a harder metal than the porous three-dimensional structure.

In some embodiments, the at least one surface feature may be comprised of a degradable material.

In some embodiments, the porous three-dimensional structure may be comprised of a degradable material.

In some embodiments, the porous three-dimensional structure may be comprised of at least two different materials.

In some embodiments, the at least one surface feature may be configured and arranged to increase the static friction of the porous three-dimensional structure.

A method for producing an orthopaedic implant is provided. The method can comprise introducing a continuous feed of metal wire onto a base surface and applying a beam at a predetermined power setting to an area where the metal wire contacts the base surface to form a porous three-dimensional structure comprising a plurality of unit cells and to form at least one surface feature that extends beyond a surface boundary of the porous-three-dimensional structure. The at least one surface feature comprises a tip region that terminates at a point.

In some embodiments, the beam may be an electron beam.

In some embodiments, the beam may be a laser beam.

In some embodiments, the method may form a plurality of surface features. In some embodiments, at least one of the plurality of surface features may be rotated at a central axis to the base at an angle different from at least one other of the plurality of surface features. In some embodiments, the plurality of surface features may be position in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

In yet another aspect, a method for producing an orthopaedic implant is provided. The method can comprise introducing a continuous feed of a polymer material embedded with a metal element onto a base surface, and applying heat to an area where the polymer material contacts the base surface to form a porous three-dimensional structure comprising a plurality of unit cells and to form at least one surface feature that extends beyond a surface boundary of the porous-three-dimensional structure. The at least one surface feature comprises a tip region that terminates at a point.

In some embodiments, the method may further include scanning the porous three-dimensional structure with a beam to burn off the polymer material. In some embodiments, the heat may be applied to the area using a heating element. In some embodiments, the heating element may be part of a furnace system. In some embodiments, the method may form a plurality of surface features. In some embodiments, at least one of the plurality of surface features may be rotated at a central axis to the base at an angle different from at least one of the plurality of surface features. In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

In a further aspect, a method for producing an orthopaedic implant is provided. The method can comprise introducing a metal slurry through a nozzle onto a base surface to form a porous three-dimensional structure comprising a plurality of unit cells and to form at least one surface feature that extends beyond a surface boundary of the porous three-dimensional structure. The at least one surface feature comprises a tip region that terminates at a point.

In some embodiments, the method may form a plurality of surface features. In some embodiments, at least one of the plurality of surface features may be rotated at a central axis to the base at an angle different from at least one other of the plurality of surface features. In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

In yet a further aspect, a method for producing an orthopaedic implant is provided. The method can comprise introducing successive layers of molten metal onto a base surface to form a porous three-dimensional structure comprising a plurality of unit cells and to form at least one surface feature that extends beyond a surface boundary of the porous three-dimensional structure. The at least one surface feature comprises a tip region that terminates at a point.

In some embodiments, the molten metal may be introduced as a continuous stream onto the base surface.

In some embodiments, the molten metal may be introduced as a stream of discrete molten metal droplets onto the base surface.

In some embodiments, the method may form a plurality of surface features. In some embodiments, at least one of the plurality of surface features may be rotated at a central axis to the base at an angle different from at least one other of the plurality of surface features. In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

In another aspect, a method for producing an orthopaedic implant is provided. The method can comprise applying and photoactivating successive layers of photosensitive polymer embedded with metal elements onto a base surface to form a porous three-dimensional structure comprising a plurality of unit cells and to form at least one surface feature that extends beyond a surface boundary of the porous three-dimensional structure. The at least one surface feature comprises a tip region that terminates at a point.

In some embodiments, the method may form a plurality of surface features. In some embodiments, at least one of the plurality of surface features may be rotated at a central axis to the base at an angle different from at least one of other of the plurality of surface features. In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

In a further aspect, a method for producing an orthopaedic implant is provided. The method can comprise depositing and binding successive layers of metal powders with a binder material to form a porous three-dimensional structure comprising a plurality of unit cells and to form at least one surface feature that extends beyond a surface boundary of the porous three-dimensional structure. The at least one surface feature comprises a tip region that terminates at a point.

In some embodiments, the method may further include sintering or melting the bound metal powder with a beam. In some embodiments, the beam may be an electron beam. In some embodiments, the beam may be a laser beam.

In some embodiments, the method may further include sintering or melting the bound metal powder with a heating element.

In some embodiments, the method may form a plurality of surface features. In some embodiments, at least one of the plurality of surface features may be rotated at a central axis to the base at an angle different from at least one other of the plurality of surface features. In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

In yet another aspect, a method for producing an orthopaedic implant is provided. The method can comprise depositing droplets of a metal material onto a base surface, and applying heat to an area where the metal material contacts the base surface to form a porous three-dimensional structure comprising a plurality of unit cells and to form at least one surface feature that extends beyond a surface boundary of the porous three-dimensional structure. The at least one surface feature comprises a tip region that terminates at a point.

In some embodiments, the metal material may be a metal slurry embedded with metallic elements.

In some embodiments, the metal material may be a metal powder.

In some embodiments, the method may form a plurality of surface features. In some embodiments, at least one of the plurality of surface features may be rotated at a central axis to the base at an angle different from at least one other of the plurality of surface features. In some embodiments, the plurality of surface features may be positioned in at least one row across the surface of the porous three-dimensional structure. In some embodiments, the surface features in the at least one row may be rotated at a central axis to the base alternately between at least a first position and a second position in a repeating pattern across the row. In some embodiments, the surface features in the at least one row may be rotated at a central axis to the base alternately between at least a first position and a second position in a non-repeating pattern across the row.

BRIEF DESCRIPTION OF THE DRAWINGS

FIG. 7 is a chart of test data noting debris formation in conjunction with various impact forces for multiple surface feature types, in accordance with various embodiments;

DETAILED DESCRIPTION

Figure 1:
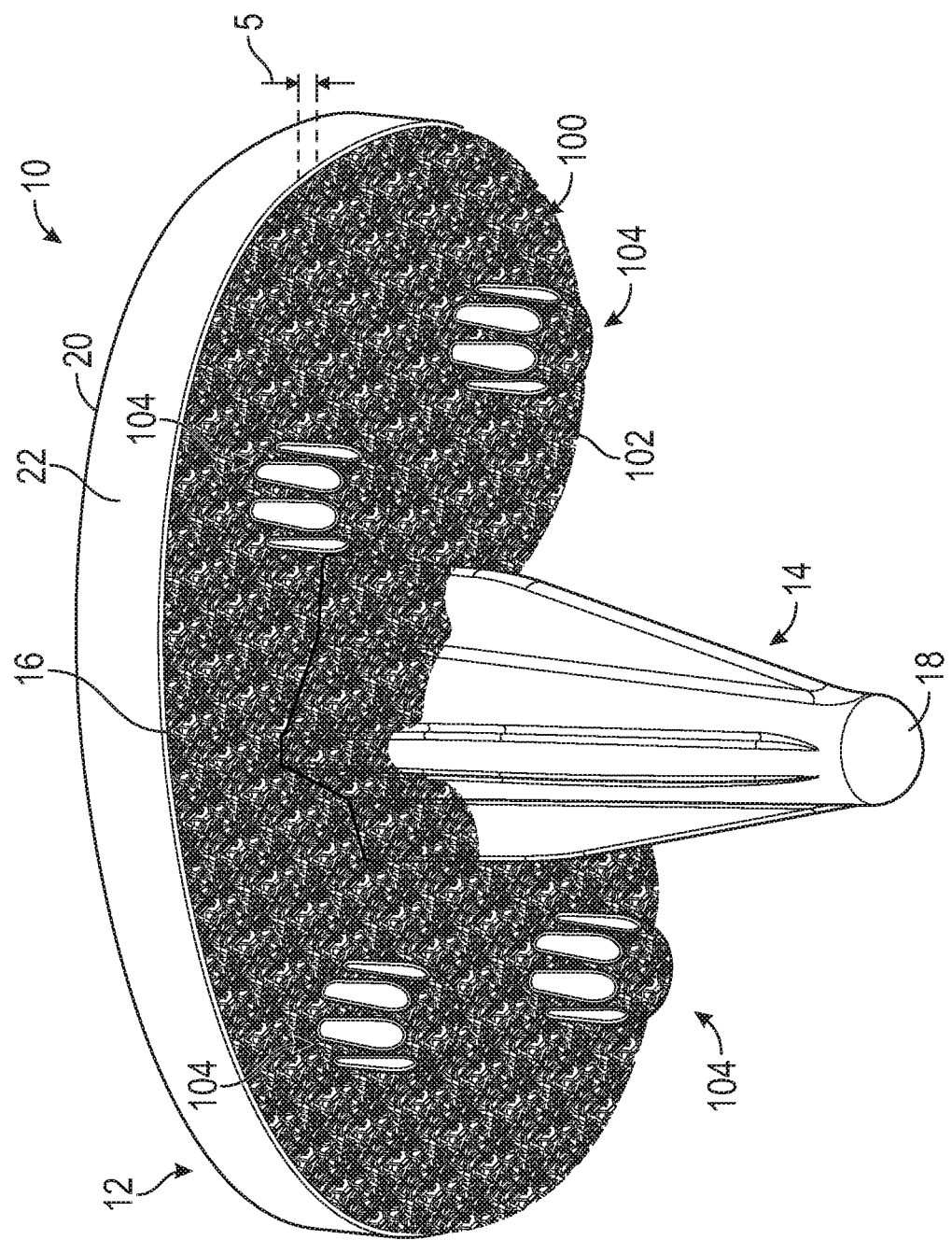
FIG. 1 is a perspective view of an orthopaedic prosthetic component.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a base, etc.) can be "on," "attached to," "connected to," or "coupled to" another element regardless of whether the one element is directly on, attached to, connected to, or coupled to the other element, there are one or more intervening elements between the one element and the other element, or the two elements are integrated as a single piece. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "bonded to" or "bonding" denotes an attachment of metal to metal due to a variety of physicochemical mechanisms, including but not limited to: metallic bonding, electrostatic attraction and/or adhesion forces.

Unless otherwise defined, scientific and technical terms used in connection with the present teachings described herein shall have the meanings that are commonly understood by those of ordinary skill in the art.

The present disclosure relates to porous three-dimensional metallic structures and methods for manufacturing them for medical applications. As described in greater detail below, the porous metallic structures promote hard or soft tissue interlocks between prosthetic components implanted in a patient's body and the patient's surrounding hard or soft tissue. For example, when included on an orthopaedic prosthetic component configured to be implanted in a patient's body, the porous three-dimensional metallic structure can be used to provide a porous outer layer of the orthopaedic prosthetic component to form a bone in-growth structure. Alternatively, the porous three-dimensional metallic structure can be used as an implant with the required structural integrity to both fulfill the intended function of the implant and to provide interconnected porosity for tissue interlock (e.g., bone in-growth) with the surrounding tissue.

In accordance with various embodiments, an orthopaedic prosthetic component is provided, the prosthetic component including a base, a porous three-dimensional structure, and at least one surface feature (hereinafter referred to as an engagement stud) extending past a surface boundary of the porous three-dimensional structure. The porous structure can include a plurality of unit cells.

The orthopaedic implant/prosthetic component, by design, can be a surgical implant configured for implantation into a patient's bone. For example, as shown in FIG. 1, an orthopaedic prosthetic component 10 is a tibial tray of a total knee arthroplasty prosthesis. The component 10 includes a platform 12 having a stem 14 extending away from its lower surface 16. The tibial stem 14 extends to a distal tip 18 and is configured to be implanted into a surgically-prepared proximal end of a patient's tibia (not shown). The platform 12 also has an upper surface 20 positioned opposite the lower surface 16 and a curved outer wall 22 that extends between the surfaces 16, 20. In the illustrative embodiment, the curved outer wall 22 is shaped to correspond to the other edge of a surgically-prepared surface on the proximal end of the patient's tibia. The platform 12 also has various engagement features (not shown) attached to the upper surface 20, which are configured to engage an insert or bearing of the total knee arthroplasty prosthesis. Exemplary engagement features, as well as exemplary other components of the knee arthroplasty prosthesis, are shown and described in U.S. Pat. No. 8,470,047, which is expressly incorporated herein by reference.

The platform 12 of the component 10 is constructed with a biocompatible metal, such as a cobalt chrome or titanium alloy, although other materials may also be used. As shown in FIG. 1, the component 10 includes a three-dimensional ingrowth body 100, which is attached to the lower surface 16 of the platform 12 such that the platform 12 provides a base for the ingrowth body 100. The ingrowth body 100 is configured to promote bone ingrowth for permanent fixation, as described in greater detail below.

In the illustrative embodiment, the ingrowth body 100 includes a plate 102 attached to the lower surface 16 of the platform 12 and a number of pegs 104 that extend outwardly from the plate 102. The ingrowth body 100 is also attached to the stem 14, which extends outwardly through the plate 102 to its distal tip 18. It should be appreciated that although a tibial prosthetic component is shown, the various porous structures described herein (including engagement stud structures described herein) can be incorporated into various orthopaedic implant designs such that the design of the implant will not impact the ability to use any of the various embodiments of engagement studs discussed herein. For example, the porous structures described herein may be included in a femoral prosthetic component similar to the femoral component shown in U.S. Pat. No. 8,470,047 or on a patella component shaped to engage the femoral prosthetic component. The porous structures may also be included in other orthopaedic implant designs, including prosthetic components for use in a hip or shoulder arthroplasty surgery.

It should be noted, for the preceding and going forward, that a base can be any type of structure capable of, for example, contacting, supporting, connecting to or with, or anchoring to or with components of various embodiments herein. Bases can include, for example, a metal or non-metal platform, a metal or non-metal tray, a metal or non-metal baseplate, a metal or non-metal structure that sits on a tray, and so on.

Figure 2:
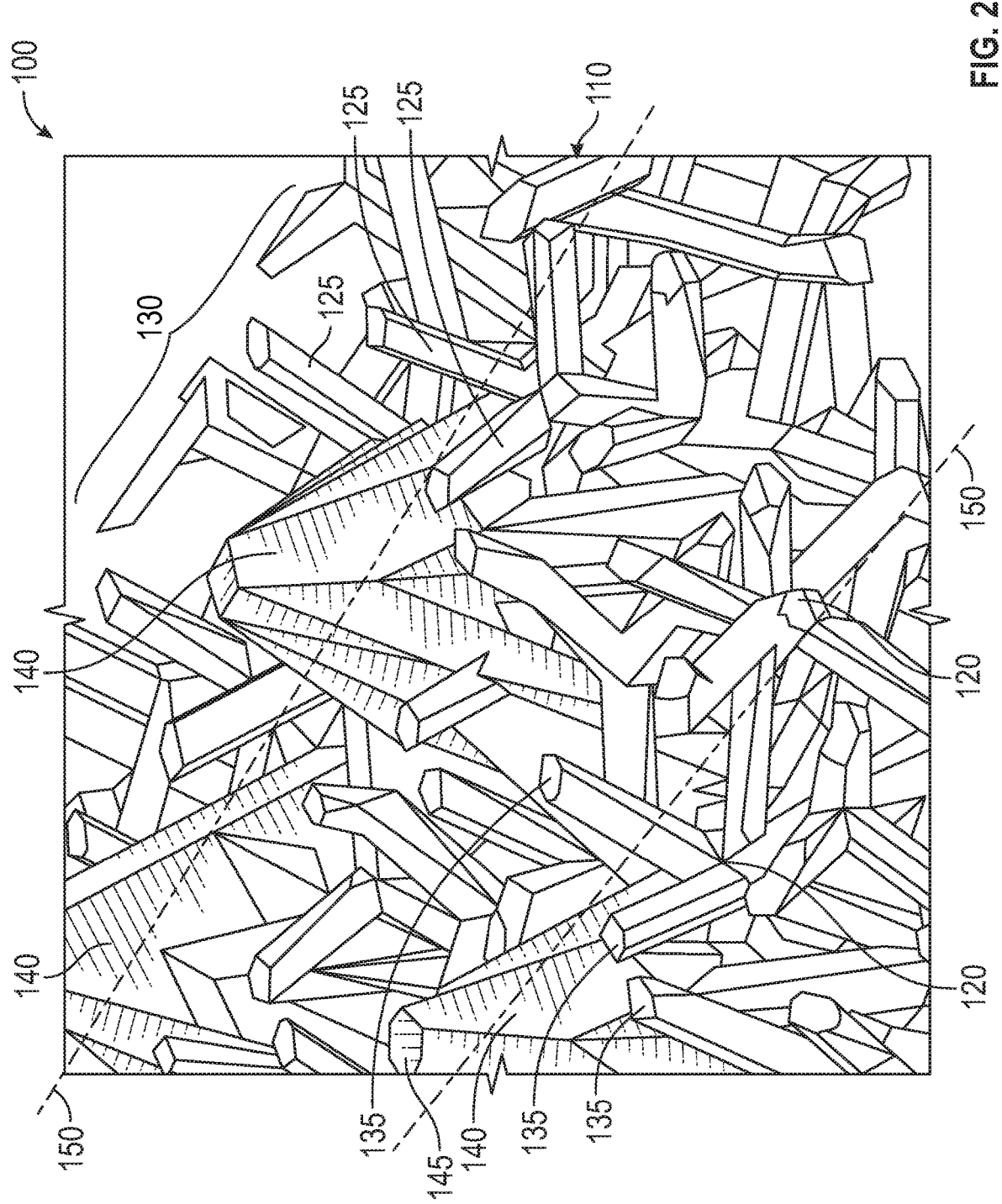
FIG. 2 is a detail perspective view of the orthopaedic prosthetic component of FIG. 1 illustrating a three-dimensional ingrowth body and a number of engagement studs of the orthopaedic prosthetic component.

Referring now to FIG. 2, the ingrowth body 100 includes a porous three-dimensional structure 110 that includes a plurality of unit cells 120, each made up multiple struts 125. The plurality of unit cells 120 are provided in repeating patterns to form the structure 110, which has a surface boundary 130 (also illustrated in FIG. 8 as surface boundary 520). The unit cells 120 define pores or voids that permit bone ingrowth after the orthopaedic prosthetic component 10 is implanted in the patient's bone, thereby promoting fixation between the component 10 and the surrounding bone tissue.

In the illustrative embodiment, the surface boundary 130 (indicated by imaginary plane in FIG. 2) is established by the farthest projected ends 135 of struts 125 and is relatively flat because the projecting struts 125 have substantially the same height. In other embodiments, the profile of the surface boundary can be relatively uneven when the projecting struts have various heights. In the case of an uneven profile, the surface boundary can be simplified, for example, to be the average of the heights of the projecting struts of the unit cells.

Strut height can be measured in various ways including, for example, the actual heights of the struts forming the surface boundary, the distance relative to a given plane parallel and below the surface boundary, or a distance from a base or base (e.g., the lower surface 16) attached to the porous structure 110, which is opposite the surface boundary 130. Such consideration of an average height can become relevant when discussed in relation to engagement studs as described below. Returning to FIG. 1, the strut height S is measured in an inferior-superior direction from the lower surface 16 of the platform 12 of the orthopaedic prosthetic component 10 to the ends 135 of the struts 125. The strut height S is equal to about 1.20 millimeters such that the porous structure 110 has a thickness of about 1.20 millimeters. It should be appreciated that, depending on the application, strut height (and hence the thickness of the porous structure) may be greater than or less than the strut height S provided in the illustrative embodiment. For example, the strut height (and thereby the thickness of porous structure) may be in a range of 0.90 millimeters to 1.60 millimeters.

The ends 135 of the struts 125 impart a surface texture at the surface boundary 130 of the plate 102 of the body 100. The ingrowth body 100 of FIG. 2 further includes a number of engagement studs 140 that impart an additional surface texture beyond the surface boundary 130 of the porous structure 110. It should be appreciated that ingrowth body 100 can have a plurality of engagement studs 140, as illustrated in FIG. 2, or only one such engagement stud. The ingrowth body 100 may include engagement studs 140 that extend from the pegs 104 in other embodiments. The engagement studs 140 can have various shapes including, for example, the cone shape illustrated in FIG. 2 having a pointed impact tip or surface 145. Each engagement stud 140 is solid in the illustrative embodiment. In other embodiments, each engagement stud 140 can be hollow, have a gap or opening, porous (porous geometry), or solid. For example, cone-shaped engagement stud 140 of FIG. 1 can be hollow, solid, or porous.

While protruding a distance from surface boundary 130 (range or height of protrusion discussed below), the cone shape adds strength to the feature by, among other things, having a narrow impact surface 145 and a wide base region, while preserving a relatively narrow profile on the portion extending past the surface boundary. The cone shape, with impact surface 145, allows for easy seating onto bone tissue. The strong base region of the cone shape also reduces the chance of the engagement studs breaking during impaction.

As shown in FIG. 2, the plurality of engagement studs 140 are arranged in multiple ordered rows on the surface boundary 130 along imaginary lines 150. It should be appreciated that the plurality of engagement studs can also be positioned in one row. The features can be randomly distributed. The distances between the individual engagement studs 140 (e.g., along a row or adjacent in a random distribution) can be substantially the same or can differ. The dimensions (e.g., height, width, length, circumference, volume, etc.) of the engagement studs 140 can be the same or can differ. The pattern of the distances and dimensions of engagement studs 140 distributed along the surface boundary can be repeated or can be random. These characteristics of the individual engagement studs 140 and the set of distributed engagement studs 140 can vary as needed. For example, the orientation, as well as the shape, of individual engagement studs 140 relative to other included engagement studs 140, can be designed and arranged to resist forces in specific directions that can differ across the surface of the tibial prosthetic component 10.

In accordance with various embodiments, the height of each engagement stud 140, relative to surface boundary 130, is in a range 0.03 and 0.30 millimeters, making each engagement stud 140 smaller than the thickness of the porous three-dimensional structure. A ratio is defined by the height of each engagement stud 140 and the thickness of the porous structure, and that ratio is less than 0.25, meaning that each engagement stud 140 is less than a quarter of the thickness of the porous structure. In other embodiments, the ratio may be in a range of 0.025 to 0.25. In still other embodiments, the ratio may be in a range of 0.025 to 0.050.

In other embodiments, the height of each engagement stud 140 can be between 0.03 millimeters and 1.00 millimeter. In still other embodiments, the height of each engagement stud 140, relative to surface boundary 130, can be between 0.10 and 0.25 millimeters. It should be appreciated that the height of each engagement stud 140 is substantially less than the length of each pegs 104, which extend a distance/height of 12.80 millimeters from the surface boundary 130. A ratio is also defined by the height of each engagement stud 140 and the distance/height of each peg, and that ratio is less than 0.02. In other embodiments, the ratio may be in a range of 0.02 to 0.08.

A plurality of engagement studs 140 can be provided with substantially similar heights or with varying heights between individual features or groups of features. The similarity and variance in engagement stud 140 heights across the overall finished product (e.g., orthopaedic implant) can be altered as necessary to provide a predetermined roughness across the implant or a specific designed roughness for specific regions of the implant.

Each engagement stud 140, in accordance with various embodiments, can be anchored or fixed to the platform 12 during manufacturing. This can be done by, for example, producing the engagement studs 140 and the platform 12 as a single integral component where the engagement stud is not a separate component physically anchored to the platform 12 but is rather machined as a projection from the surface of the platform 12. Moreover, each engagement stud can be applied to a purely solid material, such as a platform 12 or other base, to produce a product (e.g., orthopaedic implant) without any porous structure included.

As shown in FIG. 2, the engagement studs 140 are illustratively incorporated into the porous structure 110 during the manufacturing of the coating such that some struts 125 extend into (and other struts 125 extend out of) the engagement studs 140. For example, engagement studs can be added in addition to a given porous structure profile such that the engagement studs modify or do not modify the porous structure profile. Besides the existing alignment characteristics provided in accordance with various embodiments herein, incorporation of engagement studs 140 as part of the porous structure (e.g., as a single design file) could provide for further aligning the engagement studs with the porous unit cell structure so as to maximize the engagement stud/porous structure contact to increase engagement stud strength. The aligning of the engagement studs 140 with the porous unit cell structure could further minimize effects of the engagement studs 140 on the overall porosity of the porous structure, and also maximize the strength of the bond between the solid base and porous structure. The aligning of engagement studs with the porous unit cell structure can be specified such that any tissue contacting the tips of the features has a guided path to grow into the porous structure along the engagement stud.

Each engagement stud 140 can include a different material from at least one of the platform 12 and the porous three-dimensional structure 110. For example, each engagement stud 140 can include a harder material than the base/base, the porous structure 110, or both. While the porous structure and/or the base/base could be made of, for example, tantalum, stainless steel, titanium, titanium alloy or some other metal or metal alloy of lower stiffness level, the engagement stud could be made of, for example, stainless steel, cobalt chrome, a ceramic-metal composite, metal with titanium nitride or silicon carbide particles embedded therein, or some other metal or metal alloy of greater stiffness level.

Regarding the porous structure 110 composition, tantalum, polyether ether ketone, titanium and titanium alloys, for example, are used due to its excellent biocompatibility and clinical history, its ability to be treated through etching and other processes to enhance the implant-bone interface, and somewhat lower stiffness than a material like, for example, stainless steel or cobalt chrome. The lower stiffness better matches the mechanical properties of bone, leading to generally better implant-bone integration.

Alternatively and/or additionally, each engagement stud 140 can include a degradable material such as, for example, degradable magnesium alloys. This would allow the engagement studs 140 to provide an initial mechanical interlock with bone, but then erode over time as the bone becomes fully integrated with the porous structure.

Similarly, the porous structure 110 could include a degradable material in addition to its metal base material. For example, a portion of the porous structure 110 could include something degradable such as, for example, biocompatible magnesium alloys, such that as the bone grows into the porous structure, some of the struts disappear over time, thus giving more space for bone tissue to grow.

Regardless of the composition of the porous structure 110, engagement studs 140, and base, the composition can include one material (e.g., a type of metal) or at least two different materials. For example, a blend of different metals can be used for any of the components to accomplish the desired purpose as discussed above. A degradable material, as referenced above, can be used as well. In another example, different materials could be used in different portions of the component (e.g., the porous structure 110). This would allow for varying the stiffness and strength of the porous structure 110 without changing the biologically favorable pore dimensions and interconnectivity. For example, a stiffer alloy could be used at regions of high stresses to improve fatigue life of an implant.

Figure 3:
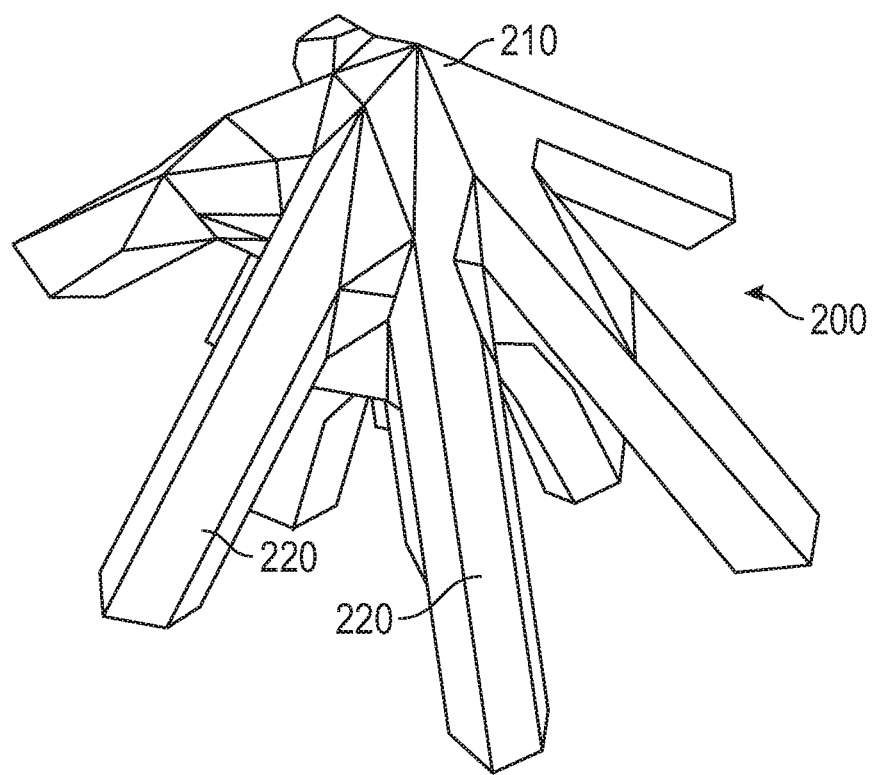
FIG. 3 illustrates a surface feature, in accordance with various embodiments.

In accordance with various embodiments, FIG. 3 illustrates an engagement stud 200 that may be included in the orthopaedic prosthetic component 10. The engagement stud 200 includes an impact surface 210 and a plurality of fins 220 that can radiate outward to form a base of the engagement stud 200. This pyramid-type shape is similar to the cone shape of FIG. 2 in that by providing a base with a broad surface that faces each direction, the engagement stud 200 is able to resist movement in those directions, including lateral motion relative to the ingrowth body. The wide base of the engagement stud 200 also provides strength and rigidity to the feature and reduces potential for debris generation upon impact into, for example, bone. Similar to the impact surface 145 of FIG. 2, the profile of impact surface 210 ensures effective embedding into, for example, bone.

The shape of fins 220 can vary. For example, the fins 220 can be a plurality of struts that intersect at a point, in this case, impact surface 210. The number of fins 220, or struts, can vary as well. In various embodiments, the engagement stud 200 can include at least three fins 220. In various embodiments, the engagement stud 200 can include between three and six fins 220. In various embodiments, the engagement stud 200 can include at least six fins 220. Another advantage of the engagement stud 200 is that by using fins 220 to provide a base, the engagement stud 200 will naturally have a degree of porosity, which helps to encourage bone growth much like the porous structure.

Figure 4:
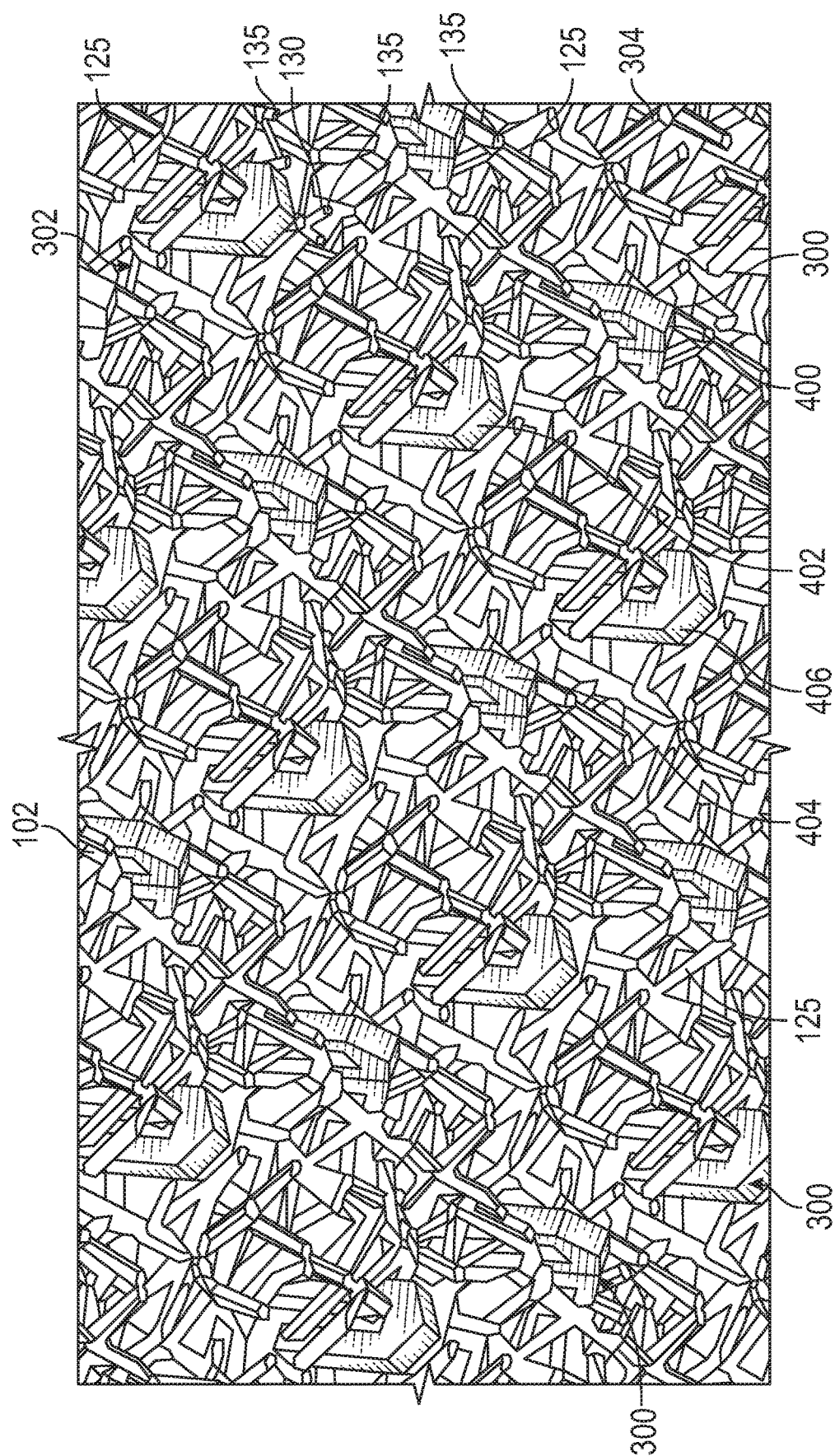
FIG. 4 illustrates a detail perspective view of another embodiment of a three-dimensional ingrowth body for inclusion in the orthopaedic prosthetic component of FIG. 1 including a plurality of engagement studs arranged in various orientations.
Figure 5:
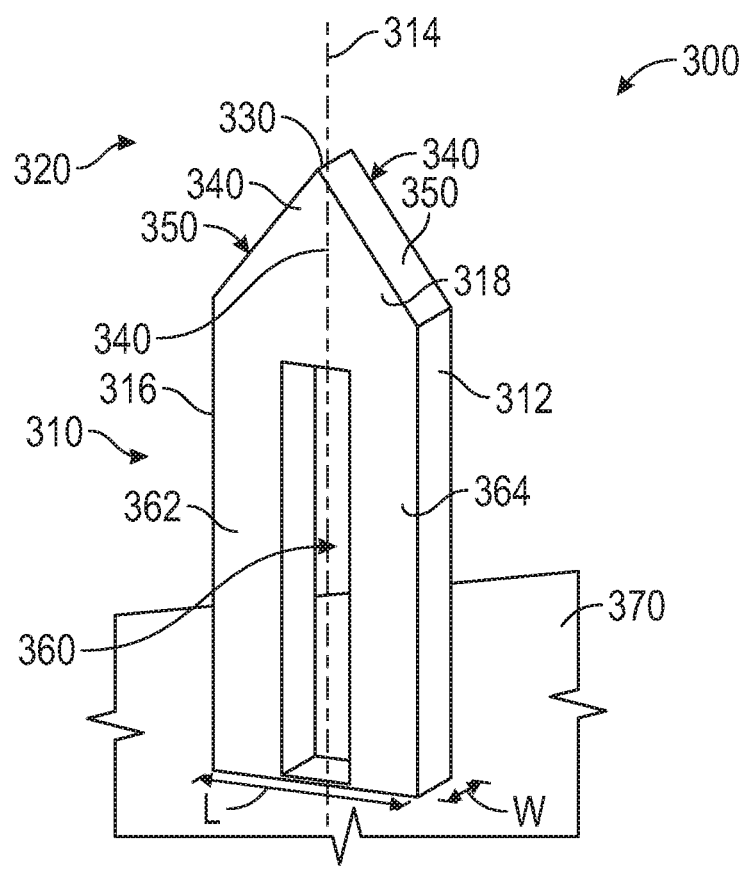
FIG. 5 illustrates one of the surface features of FIG. 4.
Figure 6:
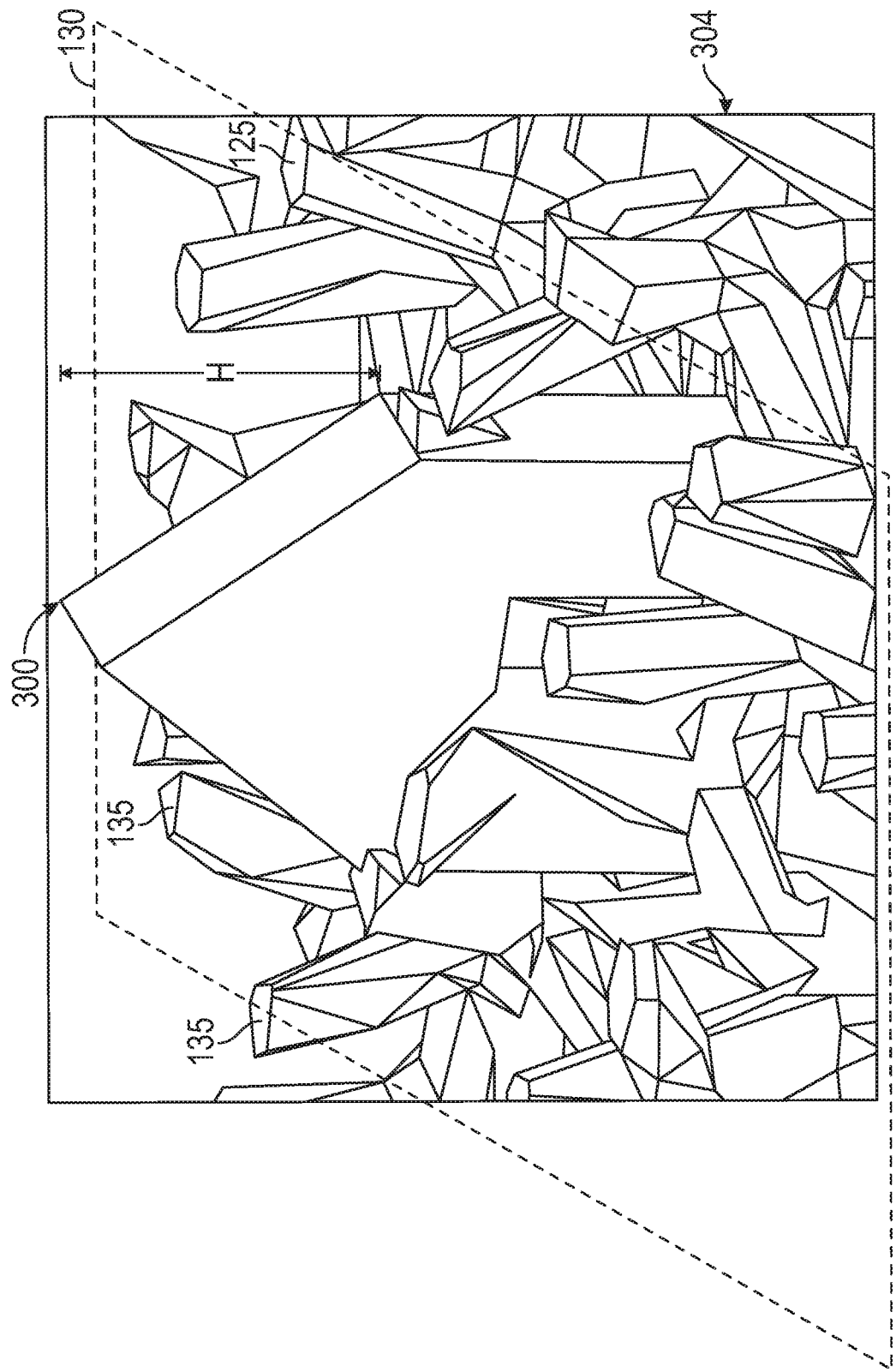
FIG. 6 is a perspective view of one of the engagement studs of FIG. 4 surrounded by the three-dimensional ingrowth body.

Referring now to FIGS. 4-6, a plurality of engagement studs (hereinafter engagement studs 300) are shown with another embodiment of a three-dimensional ingrowth body (hereinafter ingrowth body 302). Some of the features of ingrowth body 302 are similar to features described above in regard to ingrowth body 100. Reference numbers that are the same or similar to the reference numbers used in FIGS. 1-2 will be used in FIGS. 4-6 to denote similar features. The three-dimensional ingrowth body 302, like the ingrowth body 100, is attached to the lower surface 16 of the platform 12 of the orthopaedic prosthetic component 10 such that the platform 12 provides a base for the ingrowth body 302. The ingrowth body 302 is configured to promote bone ingrowth for permanent fixation and includes a plate 102 and pegs 104 (not shown), like the ingrowth body 100.

The ingrowth body 302 includes a porous structure 304 that includes a plurality of unit cells 120, each made up multiple struts 125. The plurality of unit cells 120 are provided in repeating patterns to form a three-dimensional porous structure having a surface boundary 130 (also illustrated in FIG. 8 as surface boundary 520). In the illustrative embodiment, the surface boundary 130 (illustrated by an imaginary plane in FIG. 6) is established by the farthest projected ends 135 of struts 125 and is relatively flat because the projecting struts 125 have substantially the same height.

In the illustrative embodiment, each engagement stud 300 is formed integrally with the porous structure 304 such that the engagement studs and the porous structure form a single integral component, and the struts 125 extend into and out of each engagement stud 300, as shown in FIGS. 4 and 6. It should be appreciated that in other embodiments, one or more of the engagement studs 300 may be formed with the platform 12, separate from the porous structure, such that the engagement stud(s) and the platform form a single integral component. The porous structure 304 and the engagement studs 300 are formed from a biocompatible metal such as, for example, a titanium alloy. In other embodiments, a blend of different metals or other materials may be used for any of the components.

As shown in FIG. 4, the configuration of each engagement stud 300 is identical in the illustrative embodiment. Referring now to FIG. 5, each engagement stud 300 includes a base region 310 that is attached to the lower surface of the orthopaedic prosthetic component 10 (identified as the base 370 in FIG. 5). The base region 310 includes an elongated body 312 that extends outwardly from the base 370 along a central axis 314 of the engagement stud 300 to a distal end 316. The distal end 316 of the body 312 is connected to an impaction head 318, which extends distally to an outer impact tip 330. The impaction head 318 and the outer tip 330 are sized to extend outwardly from the surface boundary 130 and define the impact region 320 of each engagement stud 300. In the illustrative embodiment, the impaction head 318 is a triangular prism.

The impaction head 318 includes a pair of flat faces 340 that extend in a proximal-distal direction. In the illustrative embodiment, the flat faces 340 extend parallel to one another. The impaction head 318 also includes a pair of sloped faces 350 that extend from the distal end 316 of the elongated body 312 to the outer tip 330 in the illustrative embodiment. Each sloped face 350 connects the opposing flat faces 340. It should be appreciated that, although the outer tip 330 is shown as having a linear edge that joins the sloped faces 350, the outer tip 330 may include a convex curved surface that joins the faces 340, 350.

As shown in FIG. 5, a slot or gap 360 is defined in the elongated body 312 such that the elongated body 312 includes a pair of parallel extending beams 362, 364. In other embodiments, the elongated body 312 of the base region 310 may be solid or include one or more gaps or slots of any of a number of sizes and shapes. For example, the gap(s) can have any three-dimensional shape including, for example, one or more squares, rectangles, ovals, circles, random shape designs, or a combination of any of these.

The engagement stud 300 is anchored to the base 370. At the base 370, the engagement stud 300 has a length L and a width W. As illustrated in FIG. 6, the engagement stud 300 projects a height H above the surface boundary 130 of the porous three-dimensional structure 304. As discussed above and as illustrated in FIG. 6, the surface boundary 130 can be defined by the outermost strut ends 135 of the porous structure 304. In the illustrative embodiment, the impaction head 318 and the outer tip 330 of the engagement stud 300 define the height H.

Returning to FIG. 4, the plurality of engagement studs 300 are arranged in a grid pattern, in rows and columns. In the illustrative embodiment, adjacent engagement studs 300, such as, for example, engagement studs 400, 402, 404, 406, are angled relative to one another and are spaced 2.0 millimeters apart in a square pattern. In that way, there are 0.25 engagement studs per square-millimeter of surface area. The engagement stud 402 is rotated 90 degrees about its central axis 314 relative to the engagement stud 400, while the engagement stud 404 extends parallel to the engagement stud 400. The engagement stud 406 is rotated 90 degrees about its central axis 314 relative to the engagement stud 400 but extends parallel to the engagement stud 402. In that way, the lugs alternate in positions. It should be appreciated that in other embodiments the engagement studs 300 may be arranged in other geometric patterns or randomly on the surface boundary 130. In other embodiments, adjacent engagement studs 300 may be positioned at other angles relative to one another.

Some known surface features are narrow or cylindrical with a spike that extends at an angle relative to the bone or other tissue. Such an angled spike embeds into bone or other tissue to assist an implant in being retained against the bone or tissue (e.g., a mechanical interlock) for which it is promoting bone ingrowth. These known surface features suffer in that they are more prone to breaking at impaction with bone or other dense tissue. Moreover, some known surface features generate significant debris during impaction. Further, to accomplish sufficient interlock, some known features are so prominent (project greatly from the implant surface), that they can hang up on the bone during impaction. Effectively, these prominent features require high forces and can give the illusion that the implant is fully seated when, in fact, it is supported only by the surface features, leaving a bone-implant gap. In so doing, the surface features may never fully implant, thereby preventing sufficient implant seating, which reduces the amount of surface area contact between the implant and bone/tissue necessary to more readily promote bone ingrowth.

The orientation and dimensions (height, length, width) of the disclosed engagement studs, according to various embodiments, can vary as needed to produce an engagement stud having several advantages. For example, various embodiments provided herein, by their design and dimensions, provide a stable mechanical interlock with bone tissue, allowing for tissue ingrowth while being less prominent (e.g., amount of feature projecting from the surface boundary that is apparent to the naked eye) to minimize opportunity for the implant to 'hang-up' on the bone, preventing implant seating, and/or reduce the surface area of the implant immediate contact with surrounding tissue. Further, for example, various embodiments provided herein, by their design and dimensions, minimize or eliminate loose or broken off portions of the coating or engagement studs that occur during implantation (e.g., impaction), during service, or even during extraction.

For example, as illustrated in FIGS. 2 and 3, various embodiments may employ a cone or pyramid-like shape. As a result, the length and width of the base region of each engagement stud may be nearly the same. Some embodiments employing such a design may actually be round at the base, thereby having a circumference rather than a length and width. These designs provide a sufficiently sharp impact surface to allow for impaction while having the strong base to minimize or eliminate breakage or lateral motion when embedded. For example, for the engagement stud 200 of FIG. 3, fins 220 can be provided at an angle of between 30 to 60 degrees from vertical (relative to the plane of the surface boundary of the porous surface). That angle helps create the sharp impact surface necessary as the fins 220 intersect at the impact surface, but also provide resistance to lateral motion. Depending on the material used, as well as the number of fins 220 used, the fin angle can vary from above. For example, for a harder material or for an engagement stud having more than the six fins illustrated in FIG. 3, the angle could be more acute (less than 30 degrees) and still achieve both the necessary impact surface as well as the sufficient strength in the overall structure.

Various other embodiments employing an engagement stud design such as that illustrated in FIGS. 4-6 can be designed to minimize prominence while maintaining the requisite sharp impact surface and structural integrity. As illustrated in FIG. 6, the engagement stud 300 can project from the boundary surface a height H, which can be, for example, the height of impact region 320. By maintaining the base region below surface boundary 135, minimal prominence is provided. The height H of the engagement stud 330, relative to surface boundary 135, is in a range between 0.03 millimeters and 1.00 millimeter. Alternatively, height can be between 0.05 and 0.30 millimeters, or can be between 0.10 and 0.25 millimeters.

To maximize advantages of the design of the engagement stud 300, a length (L) to width (W) ratio can be utilized. As illustrated in FIG. 5, the length L of the engagement stud 300 is the same between the base 370 and the impact tip 330 and is greater than the width W. By having a width (W) that is smaller than its length (L), the engagement stud 300 can have a narrow fin design that maximizes the sharpness quality of impact region 320 and, by extension, impact tip 330. In relation to width, by providing a greater length, each engagement stud 300 can provide the necessary strength in base region 310 and the impact region 320 to resist shearing forces, minimize or eliminate lateral motion, and eliminate or prevent breakage or debris formation. Therefore, in the illustrative embodiment, each engagement stud 300 has a length to width ratio of between 1.5 to 3.5. In other embodiments, each engagement stud 300 may have a length to width ratio of at least 1.5.

Depending on the application and expected hardness of bone or tissue, the ratio and height of the engagement studs can be varied as needed to provide effective implant seating while maximizing friction. This will lead to a resistance to shearing and resistance to lateral motion between the engagement stud and the impacted bone or tissue. For example, engagement studs in accordance with various embodiments herein can be utilized for applications where the implant is impacted directly onto bone, such as on a tibial baseplate or acetabular shell. In environments where there is shearing motion as well, such as on a hip stem, dimensions can be altered to minimize the shearing motion or the effects therefrom.

Regarding debris formation and avoidance, the engagement studs in accordance with various embodiments described herein (Cones, Pyramidal fins, Triangular prisms) were tested relative to known in-growth bodies (e.g., Titanium Gription®) to detect debris formation in conjunction with various impact forces. The results of this test are provided in table 700 in FIG. 7. Coupons of each engagement stud (e.g., test discs of each engagement stud provided on a porous body) was tested at low (e.g., light tap with a, for example, 1.25 lb. surgical hammer), realistic (e.g., a typical impact during surgery as observed in cadaver labs and actual surgical procedures) and high impact forces (e.g., sufficient force via a hammer to leave circular dents on the bone and dents on the backside of the tested coupons). The coupons, in this case, were approximately 0.75 inches in diameter. As observed, and provided in FIG. 7, at each force level, the engagement studs that represent examples of the various embodiments herein performed as well as the three test coupons for Titanium Gription®. Therefore, the engagement studs, which represent examples of the various embodiments herein, provide the desired resistance to debris formation.

Figure 8:
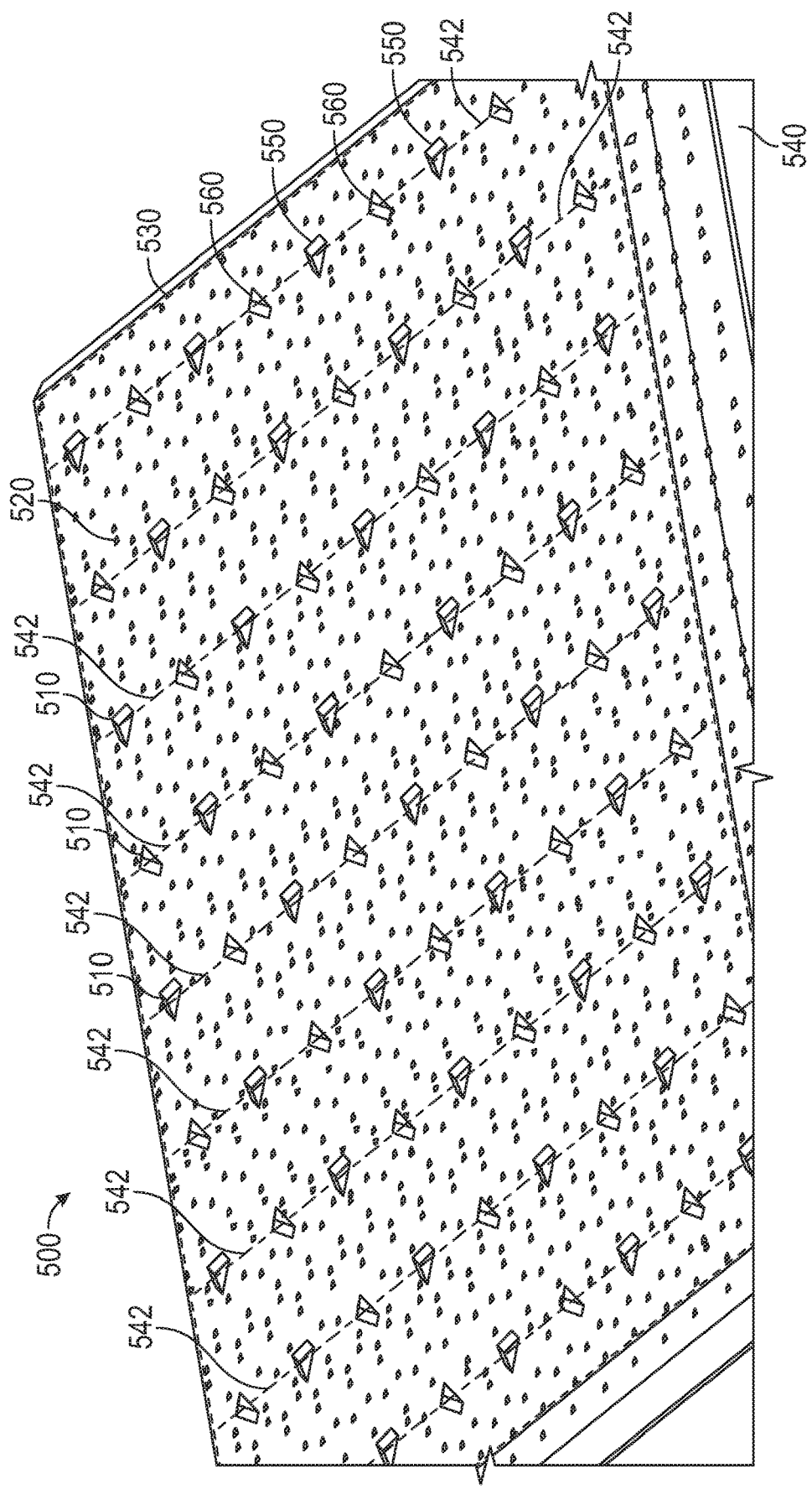
FIG. 8 is another perspective view of multiple engagement studs projecting outwardly from the surface boundary of a porous structure, in accordance with various embodiments.

As described above, the engagement studs may be arranged in a number of different patterns relative to the surface boundary of the porous structure or other surface of the implant. FIG. 8 illustrates an arrangement of a plurality of engagement studs 510 of an implant 500 in accordance with various embodiments. Each engagement stud 510 projects above a surface boundary 520 of a porous three-dimensional structure 530 of the implant 500. As stated previously, the porous structure can be provided on a tibial platform or other base 540. Alternatively, the porous structure 530 (or any of the various embodiments herein) can be free standing. The engagement studs 510 are anchored to the base 540 and integrated into the porous structure 530. Alternatively, the engagement studs can be integrated into the porous structure 530, regardless if a base is provided, or integrated into the base 540, regardless if a porous structure 530 is provided.

The engagement studs illustrated in FIG. 8 have substantially the same design as those illustrated in FIGS. 4-6. However, any of the engagement studs of the various embodiments herein can be used. The plurality of engagement studs can be positioned in at least one row along surface boundary 520. In FIG. 8, the engagement studs 510 are illustrated as being in a plurality of rows, each row being positioned on an imaginary line 542 that extends parallel to the other imaginary lines along the surface boundary 520.

Each engagement stud 510 can be oriented in the same position. As illustrated in FIG. 8, however, the engagement studs 510 can alternate between a first position 550 and a second position 560. These alternating positions can follow a pattern or can be random. Moreover, the engagement studs 510 can alternate between more than two different positions. For example, as illustrated in FIG. 8, the engagement studs 510 alternate between the first position 550 and a second position 560 in a repeating pattern across a row. Furthermore, the engagement studs 510 can alternate between the first position 550 and a second position 560 in the same or a different repeating pattern across each row. Even further, the engagement studs 510 can alternate between the first position 550 and a second position 560 in a non-repeating pattern across a row, or across each row. As such, the position of the engagement studs can follow any contemplated pattern of positions, or a random distribution of positions, with any number of different positions desired.

In accordance with various embodiments, at least one of the plurality of engagement studs 510 can be positioned at an angle relative to at least one other of the plurality of engagement studs 510. FIG. 8 illustrates one example of differing angles serving as the first and second position 550 and 560. In FIG. 8, first position and second position vary by a 90-degree rotation about the central axis 562 of each engagement stud 510 and is repeated back and forth across each row. Again, this is one example of a repeating pattern of engagement stud distribution that provides two alternating positions. Another example could include first and second positions varying by rotating the engagement studs a certain angle about the z-axis. The design flexibility for engagement stud orientation, in this case, as to rotation, could be beneficial when implanting against a non-flat bone/tissue surface. By allowing for differing positions, the design and orientation of the engagement studs can be specifically tailored to the surface profile of the bone/tissue interface impacted.

As stated above, one of the objects of an improved engagement stud is to minimize lateral motion once an engagement stud is impacted into bone/tissue. In other words, each engagement stud can be designed to increase static friction, or friction between the engagement stud and the bone or tissue material after impaction. Increased static friction allows for minimizing movement of engagement stud and bone/tissue relative to each other. Static friction can arise as the result of surface roughness features across multiple length-scales at solid surfaces. These features, known as asperities, can be present down to nano-scale dimensions and result in true solid to solid contact existing only at a limited number of points accounting for only a fraction of the apparent or nominal contact area. The linearity between applied load and true contact area, arising from asperity deformation, gives rise to the linearity between static frictional force and normal force.

Static friction force must be overcome by an applied force before an object can move. The maximum possible friction force between two surfaces before sliding begins is the product of the coefficient of static friction and the normal force. Once that applied force surpasses that value, the applied force overcomes the force of static friction and causes sliding to occur. Therefore, the higher the coefficient of static friction, the more resistant an engagement stud will be to allow sliding, or lateral motion.

Figures 9, 10:
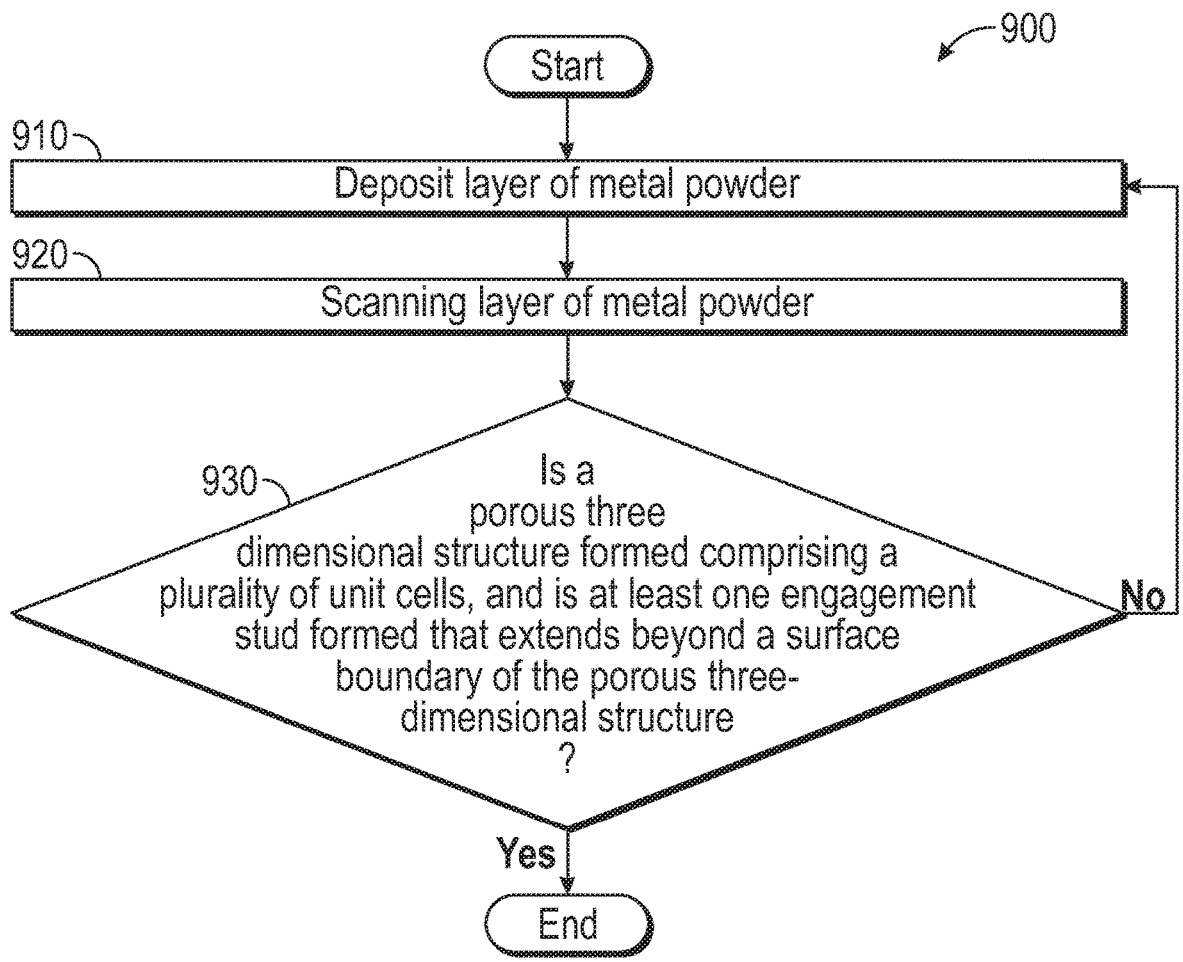
FIG. 9 is a chart of surface features and corresponding coefficient of static friction values, in accordance with various embodiments.
FIG. 10 is a flow chart illustrating a method for producing an orthopaedic prosthetic component, in accordance with various embodiments.

Referring to FIG. 9, engagement studs in accordance with various embodiments herein (Cones, Pyramidal fins, Triangular prism) were tested relative to known porous structures (Titanium Porocoat®, Titanium Gription®) and one variable without any porous structures (No Texture 3DP) for coefficient of static friction (static CoF) values. As shown in table 800 in FIG. 9, examples of the new engagement stud designs, namely Cones (see, e.g., FIG. 2), Pyramidal fins (see, e.g., FIG. 3) and Triangular prism (see, e.g., FIGS. 4-6), performed as well as the other tested variables, meaning that the new engagement stud designs provide the desired resistance to sliding consistent with the performance of known devices. Moreover, each of the new engagement studs had static CoF values over 1.0, meaning that the features have a greater friction force than its associated normal force.

As discussed in detail above and in accordance with various embodiments, orthopaedic implants can be provided that include a porous three-dimensional structure, the structure including a plurality of unit cells, and at least one engagement stud extending past a boundary of the porous three-dimensional structure. The at least one engagement stud can have a gap or opening and can comprise a plurality of fins that intersect at a point.

As discussed in detail above and in accordance with various embodiments, orthopaedic implants can be provided that include a porous three-dimensional structure, the structure including a plurality of unit cells and a plurality of engagement studs extending past a boundary of the porous three-dimensional structure. At least one of the plurality of engagement studs can be positioned at an angle relative to at least one other of the plurality of engagement studs.

In accordance with various embodiments, methods for producing an orthopaedic implant are provided. The methods can include depositing and melting successive layers of metal powders to form a porous three-dimensional structure comprising a plurality of unit cells and to form a plurality of engagement studs that extend beyond a boundary of the porous-three-dimensional structure. The plurality of engagement studs can have a gap or opening and can comprise a different metal than the metal of the porous-three-dimensional structure. Alternatively, the engagement studs can comprise the same material as the porous structure. The methods can further include providing a base, with the engagement studs anchored to the base. The methods can further include depositing and melting successive layers of metal powders onto the provided base whereby the implant includes the base, the porous structure and the plurality of engagement studs.

As described above, at least one of the plurality of engagement studs can include a plurality of fins (for example, at least three fins) that intersect at a point (e.g., an impact surface). The engagement studs can be, for example, triangle shaped or cone shaped. The engagement studs can be positioned in at least one row across the surface of the porous three-dimensional structure, or along the boundary (e.g., surface boundary) of the porous three-dimensional structure. The engagement studs can be positioned in a plurality of rows along the surface or boundary.

Additionally, the engagement studs can have any orientation or positioning relative to each other in view of the bone/tissue interface that the engagement studs will impact. For example, engagement studs (whether distributed in a row, randomly, or some other organized distribution) can alternate between at least a first position and a second position in a repeating pattern or non-repeating pattern. This positional pattern can occur across at least one row or a plurality of rows if the engagement studs are indeed distributed in rows.

Again, the engagement studs can comprise the same material as the porous structure, the base (if provided) or both. The engagement studs can, include different material than the porous structure, the base (if provided) or both. If so, the engagement studs can include a harder metal than the porous three-dimensional structure. Alternatively or in addition to the harder material, the engagement studs can include a degradable material. Likewise, the porous three-dimensional structure can include a degradable material. The porous three-dimensional structure can also include at least two different materials.

As discussed above, the engagement studs help avoid or minimize shearing or lateral motion once impacted, the engagement studs can be designed to have a high coefficient of static friction. In accordance with various embodiments, therefore, the at least one of the engagement studs can have a coefficient of static friction equal or greater than 1.0. As to height of the engagement studs, at least one of the engagement studs has a height, relative to the surface boundary, of between 0.03 and 1.00 millimeters.

Manufacturing Processes

The porous three-dimensional metallic structures disclosed above can be made using a variety of different metal component manufacturing techniques, including but not limited to: Casting Processes (casting processes involve pouring molten metal into a mold cavity where, once solid, the metal takes on the shape of the cavity. Examples include, expendable mold casting, permanent mold casting, and powder compaction metallurgy), Deformation Processes (deformation processes include metal forming and sheet metalworking processes which involve the use of a tool that applies mechanical stresses to metal which exceed the yield stress of the metal), Material Removal Processes (these processes remove extra material from the workpiece in order to achieve the desired shape. Examples of material removal processes include, tool machining and abrasive machining), and Additive Manufacturing Processes (these processes involve the use of digital 3D design data to build up a metal component up in layers by depositing successive layers of material). Additive Manufacturing Processes can include, only by way of example, powder bed fusion printing (e.g., melting and sintering), cold spray 3D printing, wire feed 3D printing, fused deposition 3D printing, extrusion 3D printing, liquid metal 3D printing, stereolithography 3D printing, binder jetting 3D printing, material jetting 3D printing, and so on. It should be appreciated, however, that additive manufacturing processes offer some unique advantages over the other metal component manufacturing techniques with respect to the manufacture of porous three-dimensional metallic structures (disclosed above) due to the complexities of the geometries and structural elements of the unit cells which comprise those types of structures.

In accordance with various embodiments, methods for producing an orthopaedic implant are provided, for example, by method 900 illustrated in FIG. 10. The methods can comprise depositing and scanning successive layers of metal powders to form a porous three-dimensional structure and to form at least one engagement stud that extends beyond a surface boundary of the porous three-dimensional structure. The at least one engagement stud can comprise a tip region that terminates at a point. The porous three-dimensional structure can be comprised of a plurality of unit cells.

The metal powders can be sintered to form the porous three-dimensional structure. Alternatively, the metal powders can be melted to form the porous three-dimensional structure.

The methods can further comprise providing a base, and forming the at least one of engagement stud on the base.

The methods can further include forming a plurality of engagement studs on the base. At least one of the plurality of engagement studs can be rotated at a central axis to the base at an angle different from at least one other of the plurality of engagement studs. The plurality of engagement studs can be positioned in at least one row across the surface of the porous three-dimensional structure, or along the boundary of the porous three-dimensional structure. Alternatively, each of the plurality of engagement studs in the at least one row can be rotated at a central axis to the base alternately between at least a first position and a second position in a repeating pattern across the row. Alternatively, each of the plurality of engagement studs in the at least one row can be rotated at a central axis to the base alternately between at least a first position and a second position in a non-repeating pattern across the row.

The at least one engagement stud can comprise a harder metal than the porous three-dimensional structure. The at least one engagement stud can comprise a degradable material. Alternatively, the porous three-dimensional structure can comprise a degradable material. The porous three-dimensional structure can comprise at least two different materials. The at least one of engagement stud can be configured and arranged to increase the static friction of the porous three-dimensional structure.

As provided in FIG. 10, step 910 includes depositing a layer of metal powder. Step 920 includes scanning a layer of metal powder. As provided in step 930, the steps 910 and 920 are repeated until the porous three-dimensional structure is formed and at least one engagement stud is formed that extends beyond a surface boundary of the porous three-dimensional structure. The porous three-dimensional structure can be comprised of a plurality of unit cells. The at least one engagement stud can be comprised of a tip region that terminates at a point.

In accordance with various embodiments, methods for producing an orthopaedic implant are provided. The methods can comprise applying a stream of metal particles at a predetermined velocity onto a base to form a porous three-dimensional structure and to form at least one engagement stud that extends beyond a surface boundary of the porous-three-dimensional structure. The porous three-dimensional structure can be comprised of a plurality of unit cells. The at least one engagement stud can include a tip region that terminates at a point. The predetermined velocity can be a critical velocity required for the metal particles to bond upon impacting the base. The critical velocity can be greater than about 340 m/s. In various embodiments, the types of metal particles that can be used include, but are not limited to, titanium, titanium alloys, stainless steel, cobalt chrome alloys, tantalum or niobium particles.

The methods can further include applying a laser at a predetermined power setting onto an area of the base where the stream of metal particles is impacting.

The methods can further comprise forming a plurality of engagement studs. At least one of the plurality of engagement studs can be rotated at a central axis to the base at an angle different from at least one other of the plurality of engagement studs. The plurality of engagement studs can be positioned in at least one row across the surface of the porous three-dimensional structure, or along the boundary of the porous three-dimensional structure. Each of the plurality of engagement studs in the at least one row can be rotated at a central axis to the base alternately between at least a first position and a second position in a repeating pattern across the row. Alternatively, each of the engagement studs in the at least one row can be rotated at a central axis to the base alternately between at least a first position and a second position in a non-repeating pattern across the row. The predetermined power setting can vary, or change over time. The power setting can range from, for example, about 50 watts to about 1000 watts.

The at least one engagement stud can comprise a harder metal than the porous three-dimensional structure. The at least one engagement stud can comprise a degradable material. Alternatively, the porous three-dimensional structure can comprise a degradable material. The porous three-dimensional structure can comprise at least two different materials. The at least one of engagement stud can be configured and arranged to increase the static friction of the porous three-dimensional structure.

In accordance with various embodiments, methods for producing an orthopaedic implant are provided. The methods can comprise introducing a continuous feed of metal wire onto a base surface, applying a beam at a predetermined power setting to an area where the metal wire contacts the base surface to form a porous three-dimensional structure and to form at least one engagement stud that extends beyond a surface boundary of the porous-three-dimensional structure. The porous three-dimensional structure can be comprised of a plurality of unit cells. The at least one engagement stud can include a tip region that terminates at a point.

The beam can be an electron beam. The beam can be a laser beam.

The methods can form a plurality of engagement studs. At least one of the plurality of engagement studs can be rotated at a central axis to the base at an angle different from at least one other of the plurality of engagement studs. The plurality of engagement studs can be positioned in at least one row across the surface of the porous three-dimensional structure, or along the boundary of the porous three-dimensional structure. Each of the engagement studs in the at least one row are rotated at a central axis to the base alternately between at least a first position and a second position in a repeating pattern across the row. Each of the engagement studs in the at least one row can be rotated at a central axis to the base alternately between at least a first position and a second position in a non-repeating pattern across the row. The predetermined power setting can vary or change over time. The power setting can range from, for example, about 50 watts to about 1000 watts. In various embodiments, the types of metal wire that can be used include, but are not limited to, titanium, titanium alloys, stainless steel, cobalt chrome alloys, tantalum or niobium wire.

In accordance with various embodiments, methods for producing an orthopaedic implant are provided. The methods can comprise introducing a continuous feed of a polymer material embedded with a metal elements onto a base surface, applying heat to an area where the polymer material contacts the base surface to form a porous three-dimensional structure and to form at least one engagement stud that extends beyond a surface boundary of the porous-three-dimensional structure. The porous three-dimensional structure can be comprised of a plurality of unit cells. The at least one engagement stud can include a tip region that terminates at a point.

The methods can further include scanning the porous three-dimensional structure with a beam to burn off the polymer material. The beam (or scanning beam) can be an electron beam. The beam (or scanning beam) can be a laser beam. Alternatively, the methods can further include placing the porous three-dimensional structure and at least one engagement stud in a heating system, such as a furnace, to burn off the polymer material. Alternatively, the polymer material can be heated and extruded through a nozzle onto the base surface. In various embodiments, the continuous feed of the polymer material can be supplied through a heated nozzle thus eliminating the need for apply heat to the area where the polymer material contacts the base surface to form the porous three-dimensional structure. In various embodiments, the types of metal elements that can be used to embed the polymer material can include, but are not limited to, titanium, titanium alloys, stainless steel, cobalt chrome alloys, tantalum and niobium.

The methods can further form a plurality of engagement studs. The plurality of engagement studs can be rotated at a central axis to the base at an angle different from at least one other of the plurality of engagement studs. The plurality of engagement studs can be positioned in at least one row across the surface of the porous three-dimensional structure, or along the boundary of the porous three-dimensional structure. Each of the engagement studs in the at least one row can be rotated at a central axis to the base alternately between at least a first position and a second position in a repeating pattern across the row. Each of the engagement studs in the at least one row can be rotated at a central axis to the base alternately between at least a first position and a second position in a non-repeating pattern across the row.

In accordance with various embodiments, methods for producing an orthopaedic implant are provided. The methods can comprise introducing a metal slurry through a nozzle onto a base surface to form a porous three-dimensional structure and to form at least one engagement stud that extends beyond a surface boundary of the porous three-dimensional structure. The porous three-dimensional structure can be comprised of a plurality of unit cells. The at least one engagement stud can include a tip region that terminates at a point. The nozzle can be heated or unheated. Alternatively, the heated nozzle is set to a temperature required to make the metal slurry feed flowable. Alternatively, evaporation is applied to bond the metallic elements of the metal slurry to the base surface. Further, the composition of the metal slurry can provide for requisite bonding without the need for additional process steps. In various embodiments, the nozzle is heated at a temperature required to bond the metallic elements of the metal slurry to the base surface.

In various embodiments, the metal slurry is an aqueous suspension containing metal particles along with one or more additive (liquid or solid) to improve the performance of the manufacturing process or the porous three-dimensional structure. In various embodiments, the metal slurry is an organic solvent suspension containing metal particles along with one or more additive (liquid or solid) to improve the performance of the manufacturing process or the porous three-dimensional structure. In various embodiments, the types of metal particles that can be utilized in the metal slurry include, but are not limited to, titanium, titanium alloys, stainless steel, cobalt chrome alloys, tantalum or niobium particles.

The methods can further form a plurality of engagement studs. At least one of the plurality of engagement studs can be rotated at a central axis to the base at an angle different from at least one other of the plurality of engagement studs. The plurality of engagement studs can be positioned in at least one row across the surface of the porous three-dimensional structure, or along the boundary of the porous three-dimensional structure. Each of the engagement studs in the at least one row can be rotated at a central axis to the base alternately between at least a first position and a second position in a repeating pattern across the row. Each of the engagement studs in the at least one row can be rotated at a central axis to the base alternately between at least a first position and a second position in a non-repeating pattern across the row.

In accordance with various embodiments, methods for producing an orthopaedic implant are provided. The methods can comprise introducing successive layers of molten metal onto a base surface to form a porous three-dimensional structure and to form at least one engagement stud that extends beyond a surface boundary of the porous three-dimensional structure. The porous three-dimensional structure can be comprised of a plurality of unit cells. The at least one engagement stud can include a tip region that terminates at a point. The molten metal can be introduced as a continuous stream onto the base surface. The molten metal can be introduced as a stream of discrete molten metal droplets onto the base surface. In various embodiments, the types of molten metals that can be used include, but are not limited to, titanium, titanium alloys, stainless steel, cobalt chrome alloys, tantalum or niobium.

The methods can form a plurality of engagement studs. At least one of the plurality of engagement studs can be rotated at a central axis to the base at an angle different from at least one other of the plurality of engagement studs. The plurality of engagement studs can be in at least one row across the surface of the porous three-dimensional structure, or along the boundary of the porous three-dimensional structure. Each of the engagement studs in the at least one row can be rotated at a central axis to the base alternately between at least a first position and a second position in a repeating pattern across the row. Each of the engagement studs in the at least one row can be rotated at a central axis to the base alternately between at least a first position and a second position in a non-repeating pattern across the row.

In accordance with various embodiments, methods for producing an orthopaedic implant are provided. The methods can comprise applying and photoactivating successive layers of photosensitive polymer embedded with metal elements onto a base surface to form a porous three-dimensional structure and to form at least one engagement stud that extends beyond a surface boundary of the porous three-dimensional structure. The porous three-dimensional structure can be comprised of a plurality of unit cells. The at least one engagement stud can include a tip region that terminates at a point. In various embodiments, the types of metal elements that can be used to embed the polymer material can include, but are not limited to, titanium, titanium alloys, stainless steel, cobalt chrome alloys, tantalum or niobium.

The methods can further comprise a plurality of engagement studs. At least one of the plurality of engagement studs can be rotated at a central axis to the base at an angle different from at least one other of the plurality of engagement studs. The plurality of engagement studs can be positioned in at least one row across the surface of the porous three-dimensional structure, or along the boundary of the porous three-dimensional structure. Each of the engagement studs in the at least one row can be rotated at a central axis to the base alternately between at least a first position and a second position in a repeating pattern across the row. Each of the engagement studs in the at least one row can be rotated at a central axis to the base alternately between at least a first position and a second position in a non-repeating pattern across the row.

In accordance with various embodiments, methods for producing an orthopaedic implant are provided. The methods can comprise depositing and binding successive layers of metal powders with a binder material to form a porous three-dimensional structure and to form at least one engagement stud that extends beyond a surface boundary of the porous three-dimensional structure. The porous three-dimensional structure can be comprised of a plurality of unit cells. The at least one engagement stud can include a tip region that terminates at a point. The methods can further include sintering or melting the bound metal powder with a beam. The beam can be an electron beam. The beam can be a laser beam. The binder material can be, for example, a polymer binder. Alternatively, the method can further include sintering the porous three-dimensional structure and at least one engagement stud in a heating system, such as a furnace. In various embodiments, the types of metal powders that can be used include, but are not limited to, titanium, titanium alloys, stainless steel, cobalt chrome alloys, tantalum or niobium powders.

The methods can further include sintering or melting the bound metal powder with a beam. The beam can be an electron beam. The beam can be a laser beam.

The methods can further form a plurality of engagement studs. At least one of the plurality of engagement studs can be rotated at a central axis to the base at an angle different from at least one other of the plurality of engagement studs. The plurality of engagement studs can be positioned in at least one row across the surface of the porous three-dimensional structure, or along the boundary of the porous three-dimensional structure. Each of the engagement studs in the at least one row can be rotated at a central axis to the base alternately between at least a first position and a second position in a repeating pattern across the row. Each of the engagement studs in the at least one row can be rotated at a central axis to the base alternately between at least a first position and a second position in a non-repeating pattern across the row.

In accordance with various embodiments, methods for producing an orthopaedic implant are provided. The methods can comprise depositing droplets of a metal material onto a base surface, applying heat to an area where the metal material contacts the base surface to form a porous three-dimensional structure and to form at least one engagement stud that extends beyond a surface boundary of the porous three-dimensional structure. The porous three-dimensional structure can be comprised of a plurality of unit cells. The at least one engagement stud can include a tip region that terminates at a point. The beam can be an electron beam. The beam can be a laser beam. The metal material can be a metal slurry embedded with metallic elements. The metal material can be a metal powder. In various embodiments, the types of metal materials that can be used include, but are not limited to, titanium, titanium alloys, stainless steel, cobalt chrome alloys, tantalum or niobium.

The methods can further form a plurality of engagement studs. The at least one of the plurality of engagement studs can be rotated at a central axis to the base at an angle different from at least one other of the plurality of engagement studs. The plurality of engagement studs can be positioned in at least one row across the surface of the porous three-dimensional structure, or along the boundary of the porous three-dimensional structure. Each of the engagement studs in the at least one row can be rotated at a central axis to the base alternately between at least a first position and a second position in a repeating pattern across the row. Each of the engagement studs in the at least one row can be rotated at a central axis to the base alternately between at least a first position and a second position in a non-repeating pattern across the row.

Although specific embodiments and applications of the same have been described in this specification, these embodiments and applications are exemplary only, and many variations are possible.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed:

1. An orthopaedic prosthetic component, comprising:
   a base,
   a porous three-dimensional structure attached to the base and configured to permit bone in-growth, the porous three-dimensional structure including a plurality of struts that are elongate along respective directions of elongation that are angularly offset with respect to the base and extend away from the base to respective farthest projected ends, the farthest projected ends defining an outer surface boundary of the porous three-dimensional structure, and
   a plurality of engagement studs that each extends out relative to the base along a respective central axis, each of the engagement studs extending outwardly from the outer surface boundary of the porous three-dimensional structure, and each of the engagement studs having a respective body and a respective impaction head that extends from the body, wherein the impaction head comprises a triangular prism having first and second parallel triangular faces that are spaced from each other, such that a distalmost outer impact tip, configured to engage a patient's bone, extends from an apex of the first triangular face to an apex of the second triangular face, wherein the plurality of engagement studs includes a first number of engagement studs, each of the first number of engagement studs being positioned at a first rotational position about its respective central axis, and a second number of engagement studs, each of the second number of engagement studs being positioned at a second rotational position about its respective central axis, wherein the second rotational position is 90 degrees offset from the first rotational position, and wherein a distance is defined between the outer surface boundary and the outer impact tip, the distance being in a range of 0.03 millimeters and 1 millimeter.

2. The orthopaedic prosthetic component of claim 1, wherein the body is elongate along the central axis in the porous three-dimensional structure.

3. The orthopaedic prosthetic component of claim 2, wherein a slot extends through the elongated body.

4. The orthopaedic prosthetic component of claim 1, wherein the engagement stud and the base are a single integral component.

5. The orthopaedic prosthetic component of claim 1, wherein the engagement stud and the porous three-dimensional structure are a single integral component.

6. The orthopaedic prosthetic component of claim 1, wherein the engagement stud is one of a plurality of engagement studs extending outwardly from the outer surface boundary of the porous three-dimensional structure, each engagement stud having an outer impact tip configured to engage a patient's bone, wherein a distance is defined between the outer surface boundary and each outer impact tip that is in a range of 0.03 millimeters and 0.30 millimeters.

7. The orthopaedic prosthetic component of claim 1, wherein the porous three-dimensional structure has a thickness, and a ratio of each distance relative to the thickness is less than 0.25.

8. The orthopaedic prosthetic component of claim 1, wherein the base includes a tibial platform configured to receive a tibial insert.

9. The orthopaedic prosthetic component of claim 8, wherein an elongated stem extends from the tibial platform to a distal tip, the elongated stem being configured to be implanted in a surgically-prepared proximal end of a patient's tibia.

10. The orthopaedic prosthetic component of claim 9, wherein the porous three-dimensional structure is attached to a distal surface of the tibial platform and the elongated stem extends outwardly through the three-dimensional structure.

11. The orthopaedic prosthetic component of claim 1, wherein at least one of each of the first and second numbers of engagement studs further comprises a base having:

opposed first and second end walls that are spaced from each other a first distance along a first direction, and first and second side walls that each extends from the first end wall to the second end wall, the first and second side walls spaced from each other a second distance along a second direction perpendicular to the first direction, the second distance less than the first distance, and wherein the first and second triangular faces are triangular in respective parallel planes that each includes the first direction and a third direction that is perpendicular to each of the first and second directions.

12. The orthopaedic prosthetic component of claim 11, wherein the first and second triangular faces are continuous with the first and second side walls, and the outer impact tip further comprises sloped faces that extend 1) from respective ones of the end walls to the edge, and 2) from the first triangular face to the second triangular face.

13. An orthopaedic prosthetic component, comprising:
a base,
a porous three-dimensional structure attached to the base, the porous three-dimensional structure being configured to permit bone in-growth and having an outer surface boundary, wherein the porous three-dimensional structure includes a plurality of struts, and
a plurality of engagement studs extending outwardly along respective central axes of the engagement studs from the outer surface boundary of the porous three-dimensional structure, each engagement stud having a body and a respective impaction head that extends from the body, wherein the impaction head comprises a triangular prism having first and second parallel triangular faces that are spaced from each other, such that an outer impact tip, configured to engage a patient's bone, extends from an apex of the first triangular face to an apex of the second triangular face, wherein each strut is shorter than each engagement stud, wherein an imaginary plane that is perpendicular to the central axes intersects the plurality of engagement studs and the plurality of struts such that respective central strut axes of the struts are angularly offset with respect to the imaginary plane, and each engagement stud of a number of the plurality of engagement studs is 1) non-circular in cross section in the imaginary plane, and 2) rotated about its central axis at an angle of 90 degrees from others of the plurality of engagement studs in the imaginary plane, and wherein the struts are elongate along the respective central strut axes.

14. The orthopaedic prosthetic component of claim 13, wherein the plurality of engagement studs are positioned on an imaginary line extending along the outer surface boundary of the porous three-dimensional structure.

15. The orthopaedic prosthetic component of claim 13, wherein the engagement studs of the number of the plurality of engagement studs is alternatingly arranged with the others of the plurality of engagement studs.

16. The orthopaedic prosthetic component of claim 13, wherein the base includes a tibial platform configured to receive a tibial insert.

17. The orthopaedic prosthetic component of claim 16, wherein an elongated stem extends from the tibial platform to a distal tip, the elongated stem being configured to be implanted in a surgically-prepared proximal end of a patient's tibia.

18. The orthopaedic prosthetic component of claim 13, wherein the struts and the engagement studs extend from the base, such that inner portions of the engagement studs are disposed within the porous three-dimensional structure, and outer portions of the engagement studs that define the impaction heads are disposed outward from the outer surface boundary of the porous three-dimensional structure.

19. The orthopaedic prosthetic component of claim 13, wherein at least one of each of the first and second numbers of engagement studs further comprises a base having:

opposed first and second end walls that are spaced from each other a first distance along a first direction, and first and second side walls that each extends from the first end wall to the second end wall, the first and second side walls spaced from each other a second distance along a second direction perpendicular to the first direction, the second distance less than the first distance, and wherein the first and second triangular faces are triangular in respective parallel planes that each includes the first direction and a third direction that is perpendicular to each of the first and second directions.

20. The orthopaedic prosthetic component of claim 19, wherein the first and second triangular faces are continuous with the first and second side walls, and the outer impact tip further comprises sloped faces that extend 1) from respective ones of the end walls to the edge, and 2) from the first triangular face to the second triangular face.

* * * * *